(12) United States Patent
Monaghan

(10) Patent No.: US 6,448,236 B1
(45) Date of Patent: Sep. 10, 2002

(54) PURINE DERIVATIVES

(75) Inventor: Sandra Marina Monaghan, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/688,497

(22) Filed: Oct. 16, 2000

(30) Foreign Application Priority Data

Oct. 14, 1999 (GB) .............................................. 9924361

(51) Int. Cl.[7] .......................... A61K 31/70; C07H 19/00

(52) U.S. Cl. .............................. 514/46; 514/45; 514/47

(58) Field of Search ............................... 536/27.2, 27.21, 536/27.3, 27.6; 514/45, 46, 47

(56) References Cited

U.S. PATENT DOCUMENTS 5,877,180 A    3/1999   Linden et al.

FOREIGN PATENT DOCUMENTS

| WO | WO 88/03147 | 5/1988 | |
| WO | 9111172 | 8/1991 | ............ A61K/9/00 |
| WO | 9402518 | 2/1994 | ........... C08B/37/16 |
| WO | WO 96/02553 | 2/1996 | |
| WO | 9855148 | 12/1998 | .......... A61K/47/48 |
| WO | WO 00/23457 | 4/2000 | |
| WO | WO 00/77018 | 12/2000 | |

OTHER PUBLICATIONS

J. Amer. Chem. Soc., 80, pp. 5168–5173, 1958.
J. Pharm. Sci., 53, p. 73, 1964.
Berge, et al., J. Pharm. Sci., 66, pp. 1–19, 1977.
J. Prakt. Chem., 321, pp. 107–111, 1979.
J. Med. Chem., 35, p. 248, 1992.
Trends in Pharmacological Sciences, 1996, 17(10), p. 364
Neuropsychopharmacology, 1997, 17, p. 82.

*Primary Examiner*—James O. Wilson
(74) *Attorney, Agent, or Firm*—Peter C. Richardson; Paul H. Ginsburg; Raymond M. Speer

(57) ABSTRACT

The present invention relates to compounds of the formula

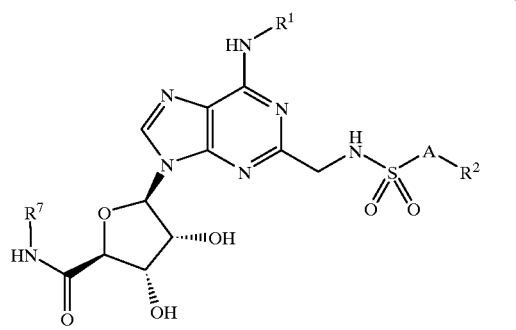

(I)

and pharmaceutically acceptable salts and solvates thereof, to processes for the preparation of, intermediates used in the preparation of, and compositions containing such compounds and the uses of such compounds as adenosine A2$a$ receptor agonists.

25 Claims, No Drawings

PURINE DERIVATIVES

REFERENCE TO COPENDING APPLICATIONS

This application is a continuation of copending prior filed international application designating the United States of America Serial No. PCT/IB00/01446 filed Oct. 6, 2000 (Attorney Docket No. PC10352), the benefit of the filing date of which is claimed, and which is incorporated herein by reference in its entirety; and corresponds to copending prior filed foreign application Great Britain Serial No. 9924361.0 filed Oct. 14, 1999 (Attorney Docket No. PC10352), the benefit of the filing date of which is claimed, and which is incorporated herein by reference in its entirety.

This invention relates to purine derivatives. More particularly, this invention relates to N-[(purin-2-yl)methyl] sulphonamide derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2^-$), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$ and HNE adversely affect the pulmonary extra-cellular matrix. The A2 receptor subtype mediating many of these responses ($O_2^-$ and $LTB_4$/HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)—induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastro-intestinal tract or a psychotic disorder, or for wound healing.

Accordingly, the present invention provides a compound of the formula:

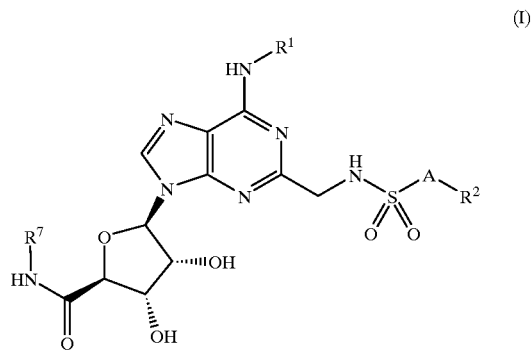

(I)

or a pharmaceutically acceptable salt or solvate thereof, wherein $R^1$ is hydrogen or $C_1$–$C_6$ alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

A is a bond or $C_1$–$C_3$ alkylene;

$R^2$ is (i) hydrogen, $C_1$–$C_6$ alkyl, $C_3$–$C_7$ cycloalkyl, phenyl or naphthyl, said $C_3$–$C_7$ cycloalkyl, phenyl or naphthyl being optionally substituted by $C_1$–$C_6$ alkyl, phenyl, $C_1$–$C_6$ alkoxy-($C_1$–$C_6$)-alkyl, $R^3R^3N$-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$, —$NR^3R^3$, —$SO_2NR^3R^3$, —$CONR^3R^3$—$NR^3COR$ or —$NR^3SO_2R^4$, with the proviso that $R^2$ is not hydrogen when A is a bond, or (ii) when A is $C_2$–$C_3$ alkylene, —$NR^8R^9$, —$OR^3$, —$COOR^3$, —$OCOR^4$, —$SO_2R^4$, —$CN$, —$SO_2NR^3R^3$, —$NR^3COR^4$ or —$CONR^3R^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^3R^3N$-($C_1$–$C_6$)-alkyl, fluoro-($C_1$–$C_6$)-alkyl, fluoro-($C_1$–$C_6$)-alkoxy, fluoro-($C_2$–$C_5$)-alkanoyl, halo, cyano, —$OR^5$, $R^6$, —$COR^5$, —$NR^5R^5$, —$COOR^5$, —$S(O)_mR^6$, —$SO_2NR^5R^5$, —$CONR^5R^5$, —$NR^5SO_2R^6$ or —$NR^5COR^6$ and optionally N-substitute by $C_1$–$C_6$ alkoxy-($C_1C_6$)-alkyl, $R^3R^3N$-($C_2$–$C_6$)-alkyl, fluoro-($C_1$–$C_6$)-alkyl, fluoro-($C_2$–$C_5$)- alkanoyl, $R^6$, —$COR^5$, —$COOR^5$, —$S(O)_mR^6$, —$SO_2NR^5R^5$ or —$CONR^5R^5$;

$R^3$ is H, $C_1$–$C_6$ alkyl, $C_3$–$C_7$ cycloalkyl or phenyl;

$R^4$ is $C_1$–$C_6$ alkyl, $C_3$–$C_7$ cycloalkyl or phenyl;

$R^5$ is H, $C_1$–$C_6$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

m is 0, 1 or 2;

"het", used in the definitions of $R^5$ and $R^6$, means C-linked pyrrolyl imidazolyl triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

$R^7$ is methyl, ethyl or cyclopropylmethyl; and either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^3R^3N$-($C_1$–$C_6$)-alkyl, fluoro-($C_1$–$C_6$)-alkyl, —$CONR^3R^3$, —$COOR^3$ or $C_2$–$C_5$ alkanoyl, and optionally substituted on a ring carbon atom not adjacent to a ring nitrogen atom by fluoro-($C_1$–$C_6$)-alkoxy, halo, —$OR^3$, cyano, —$S(O)_mR^4$, —$NR^3R^3$, —$SO_2NR^3R^3$, —$NR^3COR^4$ or —$NR^3SO_2R^4$, and said piperazin-1-yl and homopiperazin-1-yl being optionally substituted on the ring nitrogen atom not attached to A by $C_1$–$C_6$ alkyl, phenyl, $C_1$–$C_6$ alkoxy-($C_2$–$C_6$)-alkyl, $R^3R^3N$-($C_2$–$C_6$)-alkyl, fluoro-($C_1$–$C_6$)-alkyl, $C_2$–$C_5$ alkanoyl, —$COOR^4$, $C_3$–$C_8$ cycloalkyl, —$SO_2R^4$, —$SO_2NR^3R^3$ or —$CONR^3R^3$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^3R^3$, —$COOR^4$, $C_2$–$C_5$ alkanoyl or —$SO_2NR^3R^3$.

In the above definitions, halo means fluoro, chloro, bromo or iodo and alkyl, alkylene, alkanoyl and alkoxy groups containing the requisite number of carbon atoms can be unbranched or branched chain. The heterocycle as defined in $R^2$ part (iii), above may be aromatic or fully or partially saturated. The expression 'C-linked' used in the definition of $R^2$ and "het" means that the group is linked to the adjacent atom by a ring carbon atom. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 1977, 66, 1–19.

The pharmaceutically acceptable solvates of the compounds of the formula (I) include the hydrates thereof.

Also included within the present scope of the compounds of the formula (I) are polymorphs thereof.

A compound of the formula (I) may contain one or more additional asymmetric carbon atoms and therefore exist in two or more stereoisomeric forms. The present invention includes the individual stereoisomers of the compounds of the formula (I) together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$ alkyl optionally substituted by 1 or 2 phenyl group(s), said phenyl group(s) being optionally substituted by $C_1$–$C_6$ alkoxy.

Preferably, $R^1$ is $C_1$–$C_6$ alkyl substituted by 1 or 2 phenyl group(s), said phenyl group(s) being optionally substituted by $C_1$–$C_6$ alkoxy.

Preferably, $R^1$ is $C_1$–$C_4$ alkyl substituted by 1 or 2 phenyl group(s), said phenyl group(s) being optionally substituted by $C_1$–$C_4$ alkoxy.

Preferably, $R^1$ is $C_1$–$C_2$ alkyl substituted by 1 or 2 phenyl group(s), said phenyl group(s) being optionally substituted by $C_1$–$C_4$ alkoxy.

Preferably, $R^1$ is diphenylethyl or (methoxyphenyl)methyl.

Preferably, $R^1$ is 2,2-diphenylethyl or (4-methoxyphenyl)methyl.

Preferably, $R^1$ is 2,2-diphenylethyl.

Preferably, A is a bond.

Preferably, A is $C_1$–$C_3$ alkylene.

Preferably, A is $C_2$–$C_3$ alkylene.

Preferably, A is $C_2$ alkylene.

Preferably, A is —$CH_2CH_2$—.

Preferably, $R^2$ is $C_1$–$C_6$ alkyl, phenyl, naphthyl or —$NR^8R^9$, said —$NR^8R^9$ preferably being piperidin-1-yl and said phenyl being optionally substituted by phenyl.

Preferably, $R^2$ is $C_1$–$C_4$ alkyl, phenyl, naphthyl or piperidin-1-yl, said phenyl being optionally substituted by phenyl.

Preferably, $R^2$ is methyl, n-propyl, isopropyl, 2-methylprop-1-yl, phenyl, naphthyl or piperidin-1-yl, said phenyl being optionally substituted by phenyl.

Preferably, $R^2$ is methyl, n-propyl, isopropyl, 2-methylprop-1-yl, phenyl, 4-phenylphenyl, 1-naphthyl, 2-naphthyl or piperidin-1-yl.

Preferably, —A—$R^2$ is methyl, n-propyl, isopropyl, 2-methylprop-1-yl, phenyl, 4-phenylphenyl, phenylmethyl, 1-naphthyl, 2-naphthyl or 2-(piperidin-1-yl)ethyl.

Preferably, $R^7$ is ethyl.

Preferred examples of compounds of the formula (I) include those of the Examples section hereafter, including any pharmaceutically acceptable salts thereof.

All the compounds of the formula (1) can be prepared by conventional routes such as by the procedures described in the general methods presented below or by the specific methods described in the Examples section, or by similar methods thereto. The present invention also encompasses any one or more of these processes for preparing the compounds of formula (I), in addition to any novel intermediates used therein. In the general methods described, $R^1$, $R^2$, $R^7$ and A are as previously defined unless otherwise stated.

All the compounds of the formula (I) can be prepared by deprotection of a compound of the formula

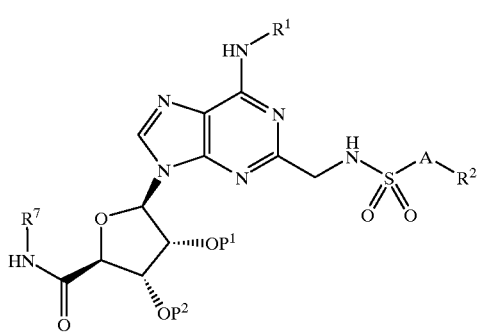

(II)

wherein $P^1$ and $P^2$ represent suitable protecting groups which may be the same or different, or $P^1$ and $P^2$ may optionally form part of the same protecting group. Examples of suitable protecting groups will be apparent to the skilled man [see for instance 'Protecting Groups in Organic Synthesis (Second Edition)', Theodora W. Green and Peter G. M. Wuts, John Wiley and Sons, 1991]. Preferred individual protecting groups are silyl (substituted with three groups selected independently from aryl and alkyl), alkanoyl and aroyl. A preferred protecting group where $P^1$ and $P^2$ form part of the same protecting group is where $P^1$ and $P^2$ taken together are $C_1$–$C_6$ alkylene. Particularly preferred individual protecting groups are benzoyl and acetyl. Particularly preferred protecting groups where $P^1$ and $P^2$ form part of the same protecting group are where $P^1$ and $P^2$ taken together are dimethylmethylene. Examples of the conditions used to achieve the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are both benzoyl, the protecting groups may be removed by treating a solution of the compound of the formula (II) in a suitable solvent, such methanol, with a base such as potassium carbonate, typically at room temperature. In a typical procedure where $P^1$ and $P^2$ taken together are dimethylmethylene, the deprotection may be carried out in the presence of a suitable acid, e.g. an aqueous mineral acid such as hydrochloric acid. In some cases, depending on the nature of the protecting groups $P^1$ and $P^2$ and the available methods for their removal, it may be expedient not to isolate compounds of the formula (II) following a prior reaction step but to deprotect them in situ. In a typical case, where $P^1$ and $P^2$ taken together are dimethylmethylene, the compound of the formula (II) is deprotected in situ in a suitable solvent such as ethanol using hydrochloric acid at a temperature of from 20 to 100° C.

The protecting groups $P^1$ and $P^2$ may be removed together in a single step or sequentially, in either order.

Compounds of the formula (II) may be prepared according to the route shown in Scheme I, wherein X is a leaving group, preferably chloro, and Ac is acetyl.

Scheme 1

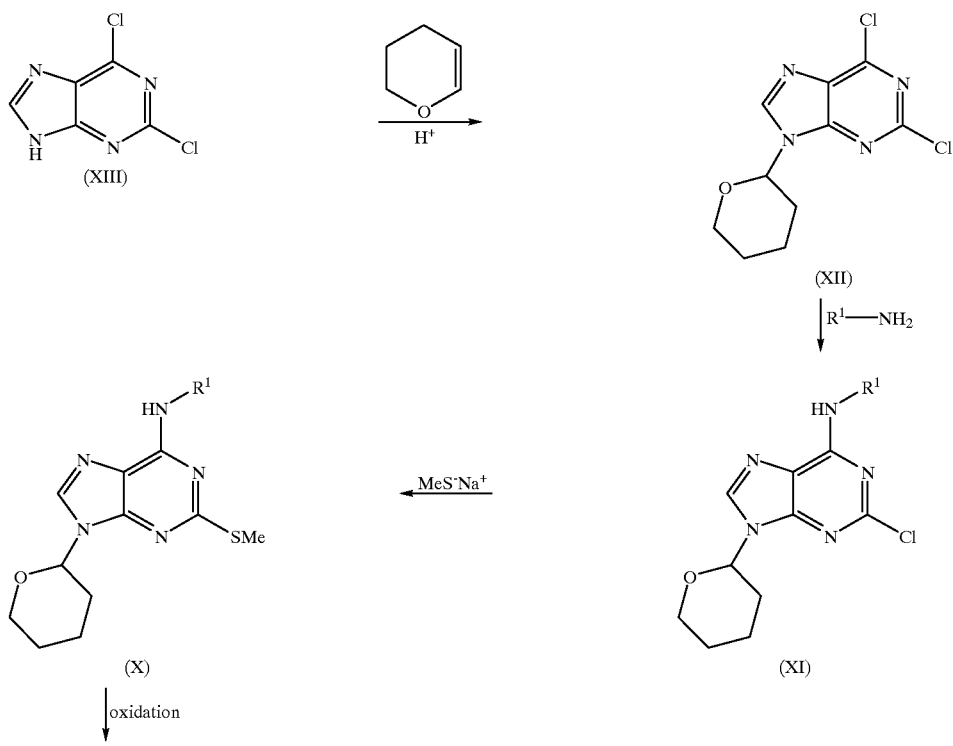

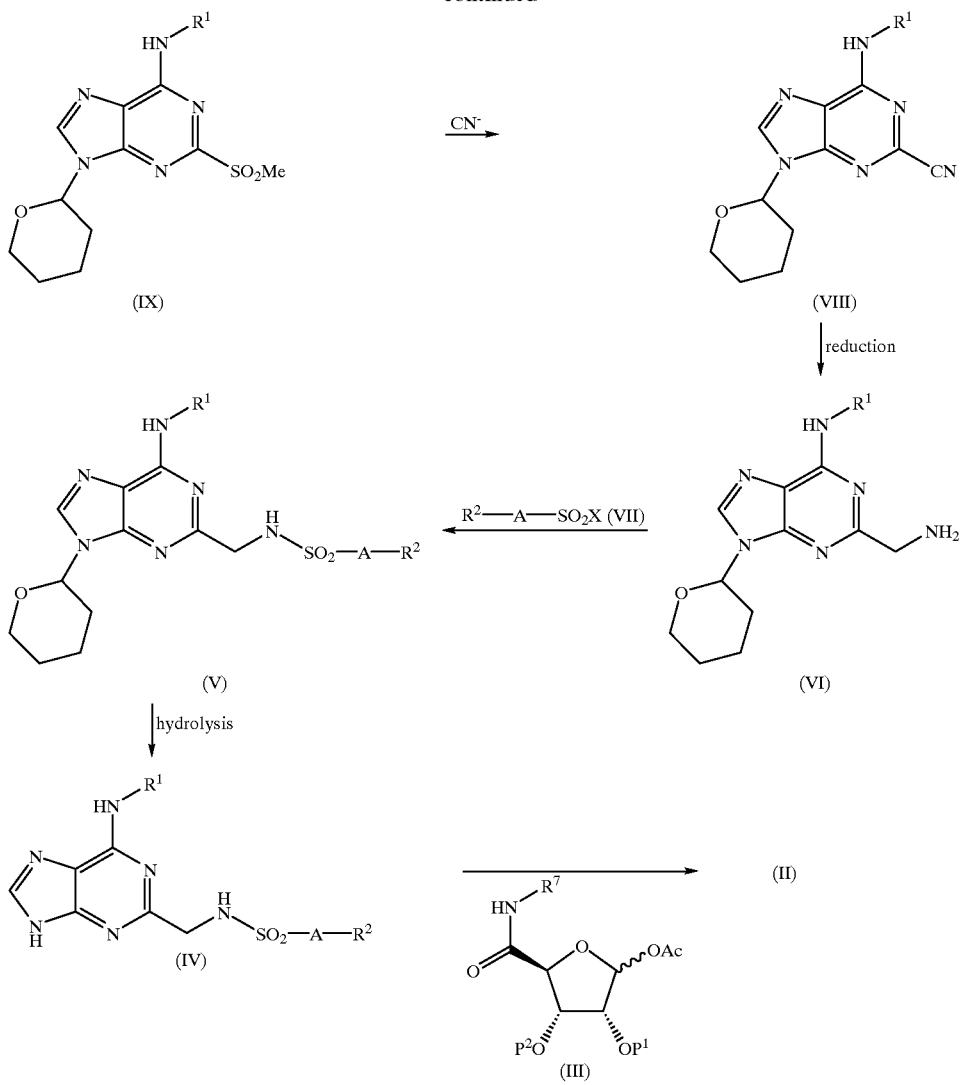

Compounds of the formula (II) may be prepared by the reaction of a compound of the formula (III) with a silyl derivative of a compound of formula (IV) according to known methods. In a typical procedure, the compound of the formula (IV) is heated as a suspension in 1,1,1,3,3,3-hexamethylsilazane under a nitrogen atmosphere until a solution has been formed. The mixture is concentrated to dryness and a solution of the residue in a suitable solvent (e.g. acetonitrile) is treated with the compound of the formula (III) and trimethylsilyl trifluoromethanesulphonate to provide a compound of the formula (II). Compounds of the formula (IV) may be prepared by the hydrolysis of a compound of the formula (V). Typically, the compound of the formula (V) is dissolved in a suitable solvent such as ethanol and treated with an acid such as hydrochloric acid. The reaction may be performed at from 0 to 100° C., preferably at from 20 to 50° C. Compounds of the formula (V) may be prepared by the sulphonylation of a compound of the formula (VI) with a compound of the formula (VII). In a typical procedure, a solution of the compound of the formula (VI) in a suitable inert solvent such as dichloromethane is treated with the sulphonylating agent. An acid acceptor such as triethylamine may be optionally added.

Compounds of the formula (VI) may be prepared by the reduction of a compound of formula (VIII). The reduction may be carried out with any suitable hydride reducing agent or by hydrogenation. In a typical procedure, a solution of the compound of the formula (VIII) in a suitable solvent such as ethanol is saturated with ammonia gas, treated with an appropriate hydrogenation catalyst such as Pearlmann's catalyst and pressurised with hydrogen, preferably to 414 kPa (60 psi). Compounds of the formula (VIII) may be prepared by reacting a compound of the formula (IX) with a source of cyanide anion such as potassium cyanide. The reaction is typically carried out in a solvent such as N,N-dimethylformamide at an elevated temperature. Compounds of the formula (IX) may be prepared by the oxidation of a compound of the formula (X). In a typical procedure, an aqueous solution of potassium peroxymonosulphate is added to a solution of the compound of the formula (X) and sodium hydrogencarbonate in a suitable solvent, such as a mixture of water and acetone. Compounds of the formula (X) may be prepared by the displacement of chloride in a compound of the formula (XI) with thiomethoxide. Typically, the reaction is carried out in a polar solvent such as N,N-dimethylformamide, at elevated temperatures and under a blanket of nitrogen. Thiomethoxide may be used in the form of an alkali metal salt such as sodium thiomethoxide. Compounds of the formula (XI) may be prepared by the reaction of a compound of the formula (XII) with an appropriate primary amine. Typically, a solution of the dichloropurine (XII) in a suitable solvent such as isopropyl alcohol is treated with such an amine and heated, preferably under reflux. An acid acceptor such as N-ethyl—N-isopropyl-2-propanamine may optionally be added. Compound (XII) may be prepared by reaction of 2,6-dichloro-9H-purine (XIII) with 2,3-dihydropyran in a suitable solvent such as ethyl acetate and in the presence of an acid catalyst such as 4-toluenesulphonic acid, usually at an elevated temperature.

Compounds of the formula (II) may also be prepared by the reaction of an amine of the formula (XIV) with a sulphonylating agent of the formula (VII) as shown in Scheme 2, wherein X is a leaving group, preferably chloro, Ac is acetyl and $P^1$ and $P^2$ are as defined above.

reducing agent or by hydrogenation. In a typical procedure, where $P^1$ and $P^2$ taken together are dimethylmethylene, a solution of the compound of formula (XV) in a suitable solvent such as ethanol is saturated with ammonia gas, treated with an appropriate hydrogenation catalyst such as 5% w/w palladium on charcoal and pressurised with hydrogen, preferably to about 1034 kPa (150 psi). Compounds of the formula (XV) may be prepared by the reaction of a compound of the formula (III) with a compound of formula (XVI) according to known methods. In a typical procedure, a mixture of the compound of the formula (XVI), the compound of the formula (III) and iodine is heated at about 150° C. under reduced pressure. With regard to the conditions to be employed in later steps, it may be appropriate to change the protecting groups $P^1$ and $P^2$ in compounds of the formula (XV). Alternative, suitable protecting groups are well-known to the skilled person [e.g. 'Protecting Groups in Organic Synthesis (Second Edition)', Theodora W. Green and Peter G. M. Wuts, John Wiley and Sons,

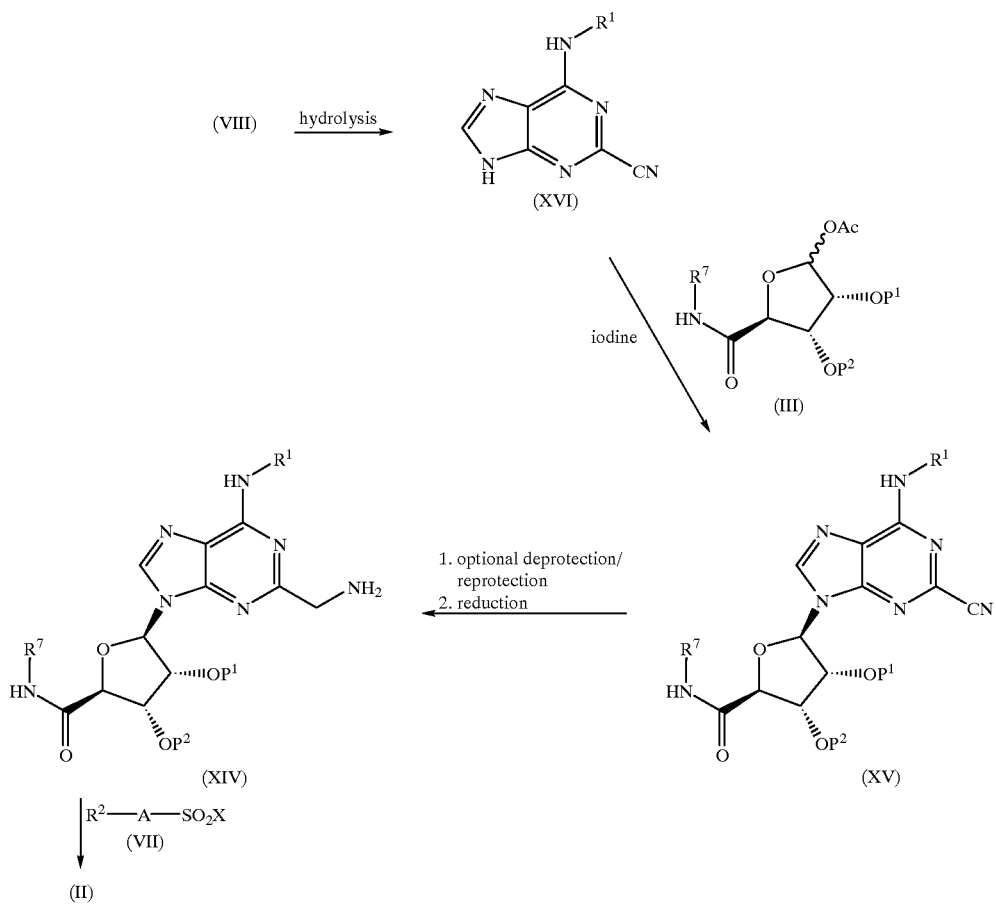

Scheme 2

In a typical procedure, a solution of the compound of the formula (XIV) in a suitable inert solvent such as dichloromethane is treated with the compound of the formula (VII). An acid acceptor such as triethylamine may optionally be added. Compounds of formula (XIV), where $P^1$ and $P^2$ taken together are dimethylmethylene, for example, may be prepared by reduction of a compound of formula (XV). The reduction may be carried out with any suitable hydride 1991]. In a typical case, if $P^1$ and $P^2$ in a compound of the formula (XV) are both benzoyl, then these protecting groups may be vulnerable to the reducing conditions employed in the next step. In this case, a solution of the compound of the formula (XV) where $P^1$ and $P^2$ are both benzoyl in a suitable solvent such as ethanol may be saturated with ammonia to give a compound of the formula (XV) wherein $P^1$ and $P^2$ are replaced by H which may be subsequently reprotected with more appropriate functionality. For instance, the compound of the formula (XV) wherein $P^1$ and $P^2$ are replaced by H may be dissolved in acetone and the resulting solution treated with 2,2-dimethoxypropane and 10-camphorsulphonic acid to give a compound of the formula (XV) wherein $P^1$ and $P^2$ taken together are dimethylmethylene. Compounds of formula (XVI) may be prepared by the hydrolysis of a compound of the formula (VIII). Typically, the compound of the formula (VII) is dissolved in a suitable solvent such as ethanol and treated with an acid such as hydrochloric acid.

Compounds of the formula (III), used in Schemes 1 and 2, may be prepared as shown in Scheme 3 wherein Ac is acetyl and $P^1$ and $P^2$ are as defined above.

Scheme 3

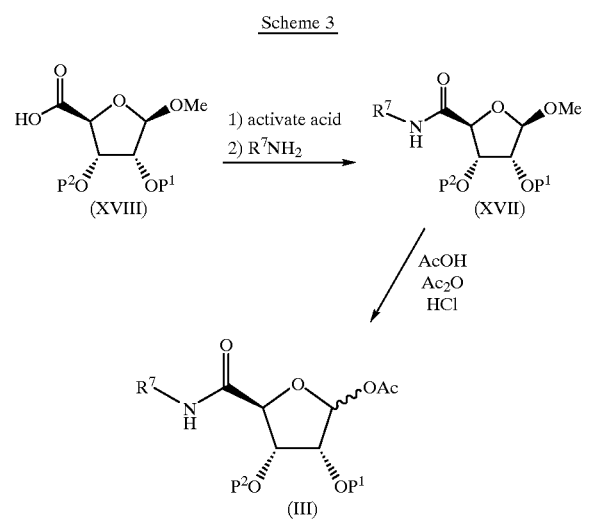

Compounds of the formula (III) may be prepared by the treatment of a compound of the formula (XVII) with a mixture of acetic acid, acetic anhydride and a strong acid such as hydrochloric acid, preferably with cooling (typically to −10° C.). Compounds of the formula (XVII) may be prepared from an acid of the formula (XVIII) by activation of the acid as, for example, an acid chloride and treatment of this activated intermediate with an appropriate primary amine. In a typical procedure, a compound of the formula (XVIII) is dissolved in a suitable inert solvent (e.g. dichloromethane) and treated with oxalyl chloride and a catalytic amount of N,N-dimethylformamide. After removal of excess solvent and reagent by evaporation under reduced pressure, the residue is dissolved in a suitable solvent, such as anhydrous dichloromethane and treated with the appropriate primary amine. With regard to the conditions employed in later steps, it may be appropriate to switch the protecting groups $P^1$ and $P^2$ in compounds of the formula (XVII). Alternative, suitable protecting groups are well-known to the skilled person [e.g. 'Protecting Groups in Organic Synthesis (Second Edition)', Theodora W. Green and Peter G. M. Wuts, John Wiley and Sons, 1991]. In a typical case, a solution of the compound of the formula (XVII) wherein Pt and $P^2$ taken together are dimethylmethylene in a suitable solvent such as methanol may treated with an acid such as pyridinium para-toluenesulphonate to give a compound of the formula (XVII) wherein $P^1$ and $P^2$ are both replaced by H which may be subsequently reprotected with other functionality. For instance, the compound of the formula (XVII) wherein $P^1$ and $P^2$ are both replaced by H may be dissolved in a suitable solvent such as dichloromethane and the resulting solution may be treated with an acid acceptor, such as pyridine and benzoyl chloride to give a compound of the formula (XVII) wherein $P^1$ and $P^2$ are each benzoyl. Compounds of the formula (XVIII) are known in the art (see for example in J. Amer. Chem. Soc., 1958, 80, 5168).

All the compounds of the formula (I) may also be prepared by the sulphonylation of a compound of the formula (XIX) with a compound of the formula (VII) as shown in Scheme 4 wherein X is a leaving group, preferably Cl and $P^1$ and $P^2$ are as previously defined.

Scheme 4

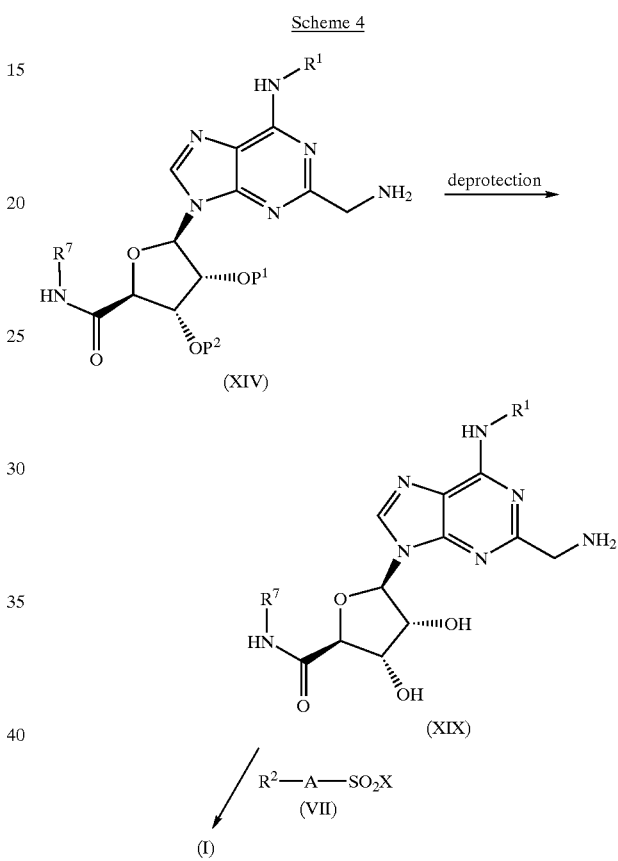

In a typical procedure, a solution of the compound of the formula (XIX) in a suitable inert solvent such as dichloromethane is treated with the sulphonylating agent of the formula (VII). An acid acceptor such as triethylamine may optionally be added. Compounds of the formula (XIX) may be prepared by the deprotection of a compound of the formula (XIV). Examples of the conditions used to achieve the deprotection are well known in the art [see for instance 'Protecting Groups in Organic Synthesis (Second Edition)', Theodora W. Green and Peter G. M. Wuts, John Wiley and Sons, 1991]. In a typical procedure, where $P^1$ and $P^2$ are both benzoyl, the protecting groups may be removed by treating a solution of the compound of the formula (II) in a suitable solvent, such methanol, with a base such as potassium carbonate, typically at room temperature. In a typical procedure where $P^1$ and $P^2$ taken together are dimethylmethylene, the deprotection may be carried out in the presence of a suitable acid, e.g. in aqueous mineral acid such as hydrochloric acid. Compounds of the formula (I) in which A is —$CH_2CH_2$— and $R^2$ is —$NR^8R^9$ may also be prepared by the reaction of a compound of the formula- (XIX) with 2-chloroethanesulfonyl chloride to give an intermediate of the formula (XX)

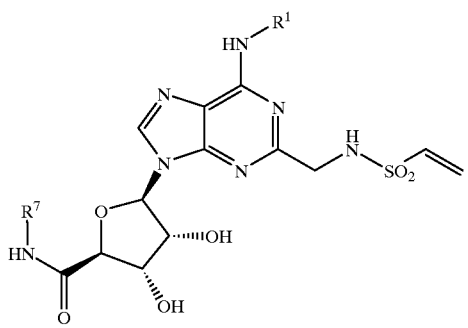

The intermediate of the formula (XX) is then treated with a compound of the formula $$R^8R^9NH \quad (XXI)$$

in which $R^8$ and $R^9$ are as defined above, to give a compound of the formula (I). The two steps may be carried out with or without isolation of the intermediate of the formula (XX). In a typical procedure, where the intermediate of the formula (XX) is not isolated, a solution of the compound of the formula (XIX) in a suitable solvent, such as acetonitrile, is treated with chioroethanesulfonyl chloride and a base, such as pyridine. When a substantially complete reaction has taken place (as judged by thin layer chromatography) a compound of the formula (XXI) is added and the reaction mixture is heated, preferably under reflux. Compounds of the formula (XXI) are either commercially available or easily prepared by techniques well known to the skilled person. Compounds of the formula (I) may also be interconverted using conventional functional group interconversion techniques. All of the reactions and the preparations of novel starting materials used in the preceding methods are conventional and appropriate reagents and reaction conditions as well as procedures for isolating the desired products will be well-known to persons skilled in the art with reference to literature precedents and the Examples and Preparations sections below. pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice. For example, the compounds of the formula (I) can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intraarterially, intraperitoneally, intrathecally, intraventricularly, intrastemally, intracranially, intramuscularly or subcutaneously, or they may be administered by infusion techniques. They are best used in the form of a sterIle aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art. For oral and parenteral administration to human patients, the daily dosage level of the compounds of the formula (I) will usually be from 0.01 to 100 mg/kg, preferably from 0.1 to 100 mg/kg (in single or divided doses).

Thus tablets or capsules of the compound of the formula (I) may contain from 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 to 4000 μg of a compound of the formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered, for example, by the use of a skin patch.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

Thus the invention provides:

(i) a compound of the formula (I) or a pharmaceutically acceptable salt or solvate thereof;
(ii) a process for the preparation of a compound of the formula (I) or a pharmaceutically acceptable salt or solvate thereof;
(iii) a pharmaceutical composition including a compound of the formula (I) or a pharmaceutically acceptable salt or solvate thereof, together with a pharmaceutically acceptable excipient, diluent or carrier;
(iv) a compound of the formula (I) or a pharmaceutically acceptable salt, solvate or composition thereof, for use as a medicament;
(v) the use of a compound of the formula (I) or of a pharmaceutically acceptable salt, solvate or composition thereof, for the manufacture of a medicament to treat a disease for which a A2a receptor agonist is indicated;
(vi) the use of a compound of the formula (I) or of a pharmaceutically acceptable salt, solvate or composition thereof, for the manufacture of an anti-inflammatory agent;
(vii) the use of a compound of the formula (I) or of a pharmaceutically acceptable salt, solvate or composition thereof, for the manufacture of a medicament for the treatment of a respiratory disease;
(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;
(ix) the use of a compound of the formula (I) or of a pharmaceutically acceptable salt, solvate or composition thereof, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-*Heliobacter pylori* gastritis, non-steroidal anti-inflammatory drug-induced damage to the gastro-intestinal tract or a psychotic disorder, or for wound healing;
(x) a method of treatment of a mammal, including a human being, to treat a disease for which a A2a receptor agonist is indicated including treating said mammal with an effective amount of a compound of the formula (I) or with a pharmaceutically acceptable salt, solvate or composition thereof;
(xi) a method of treatment of a mammal, including a human being, to treat an inflammatory disease including treating said mammal with an effective amount of a compound of the formula (I) or with a pharmaceutically acceptable salt, solvate or composition thereof;
(xii) a method of treatment of a mammal, including a human being, to treat a respiratory disease including treating said mammal with an effective amount of a compound of the formula (I) or with a pharmaceutically acceptable salt, solvate or composition thereof;
(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;
(xiv) a method of treatment of a mammal, including a human being, to treat septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohns disease, inflammatory bowel disease, *Helicbacter pylori*-gastritis, non-*Heliobacter pylori* gastritis, non-steroidal anti-inflammatory drug-induced damage to the gastro-intestinal tract or a psychotic disorder, or for wound healing, including treating said mammal with an effective amount of a compound of the formula (I) or with a pharmaceutically acceptable salt, solvate or composition thereof; and
(xv) certain novel intermediates disclosed herein.

The following Examples Illustrate the preparation of the compounds of the formula (I):

EXAMPLE 1

(2S,3S,4R,5R)-5-{2-{[(Benzylsulfonyl)amino]methyl}-6-[(2,2-diphenylethyl)amino]-9H-purin-9-yl}-N-ethyl-3,4dihydroxytetrahydro-2-furancarboxamide

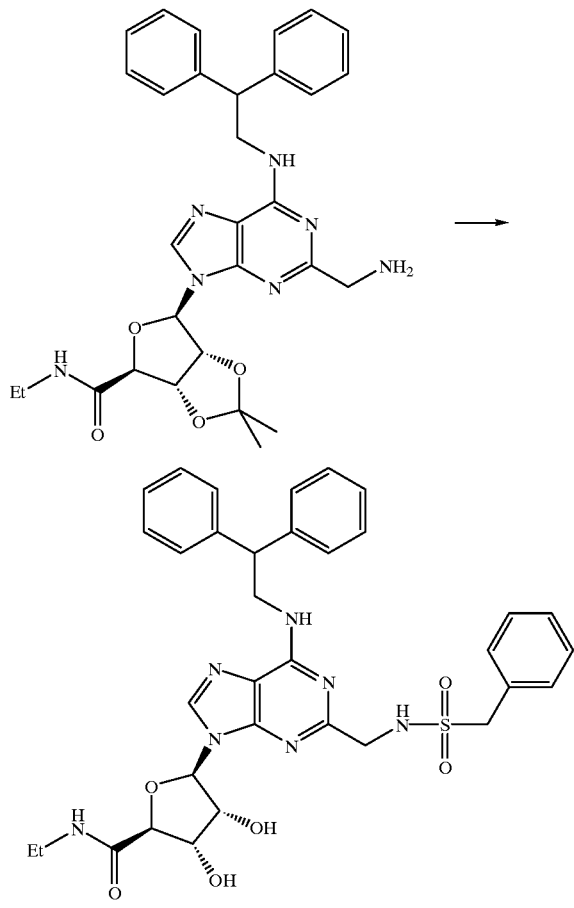

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (120 mg, 0.21 mmol) and triethylamine (0.04 ml, 0.29 mmol) in anhydrous dichloromethane (2 ml) was treated with phenylmethylsulphonyl chloride (45 mg, 0.24 mmol). The mixture was stirred at room temperature for 2 hours. The solvent was removed under reduced pressure and the residue dissolved in ethanol (1 ml). Hydrochloric acid (1M, 1 ml) was added to the solution and the mixture was heated at 60° C. for 8 hours. The solvent was removed under reduced pressure and the residue was azeotroped with ethanol (×2). The residue was purified by column chromatography on silica gel eluting with a gradient system of dichloromethane methanol (95:5 by volume) gradually changing to dichloromethane: methanol (90:10 by volume) to give a solid which was triturated with diethyl ether, diluted with pentane, filtered and dried to afford the title compound as a white solid (92 mg).

$^1$H-NMR (CDCl$_3$+2 drops DMSO-d$_6$) δ: 7.79 (1H, br s), 7.13–7.38 (16H, m), 5.94 (1H, br s), 5.81 (2H, m), 4.87 (1H, br m), 4.70 (1H, q), 4.60 (1H, m), 4.49 (1H, d), 4.42 (1H, d), 4.16–4.36 (7H, m), 3.31 (1H, m), 3.12 (1H, m), 1.02 (3H, t).

Analysis: Found C, 60.67; H, 5.63; N, 14.30%; C$_{34}$H$_{37}$N$_7$O$_6$S requires C, 60.79; H, 5.55; N, 14.60%.

EXAMPLE 2

(2S,3S,4R,5R)-5-(6-[(2,2-Diphenylethyl)amino]-2-{[(propylsulfonyl)amino]methyl}-9H-purin-9-yl)-ethyl-3,4-dihydroxytetrahydro-2-furancarboxamide

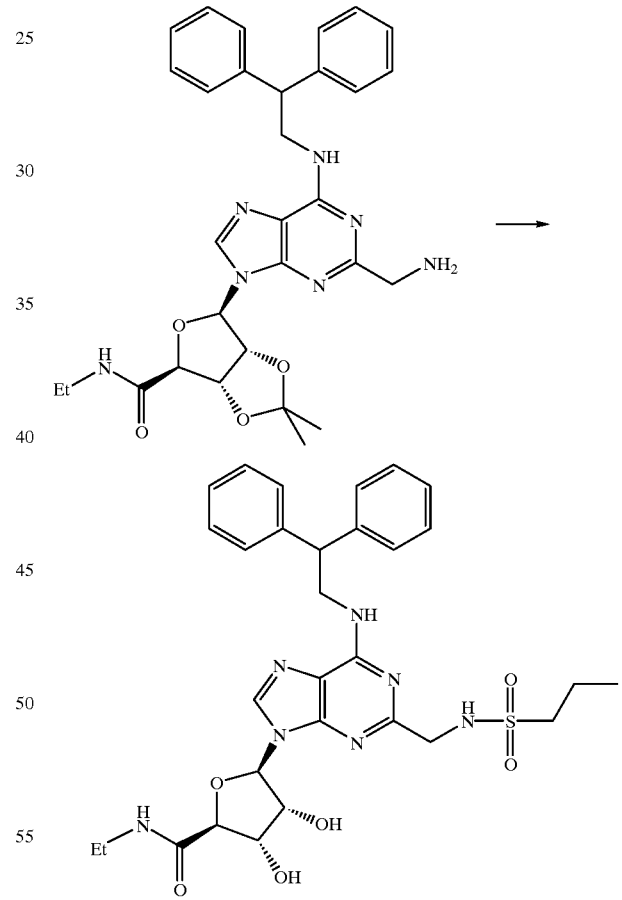

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of 1-propanesulphonyl chloride (40 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1 M, 1 ml) and heated at 60° C. for 4 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether, diluted with pentane, filtered and dried to afford the title compound as a solid (90 mg).

$^1$H-NMR (CDCl$_3$+1 drop DMSO-d$_6$) δ: 7.80 (1H, br s), 7.15–7.35 (10H, m), 5.91 (2H, m), 5.75 (1H, t), 4.77 (3H, m), 4.52 (1H, m), 4.18–4.44 (5H, m), 3.39 (1H, m), 3.22 (1H, m), 2.99 (2H, t), 1.83 (2H, m), 1.06 (3H, t), 0.98 (3H, t).

Analysis:Found C, 57.51; H, 6.00; N, 15.54%; C$_{30}$H$_{37}$N$_7$O$_6$S requires C, 57.77; H, 5.98; N, 15.72%.

EXAMPLE 3

(2S,3S,4R,5R)5-(6-[(2,2-Diphenylethyl)amino]-2-{[(isopropylsulfonyl)amino]methyl}-9H-purin-9-yl)-N-ethyl-3,4-dihydroxytetrahydro-2-furancarboxamide

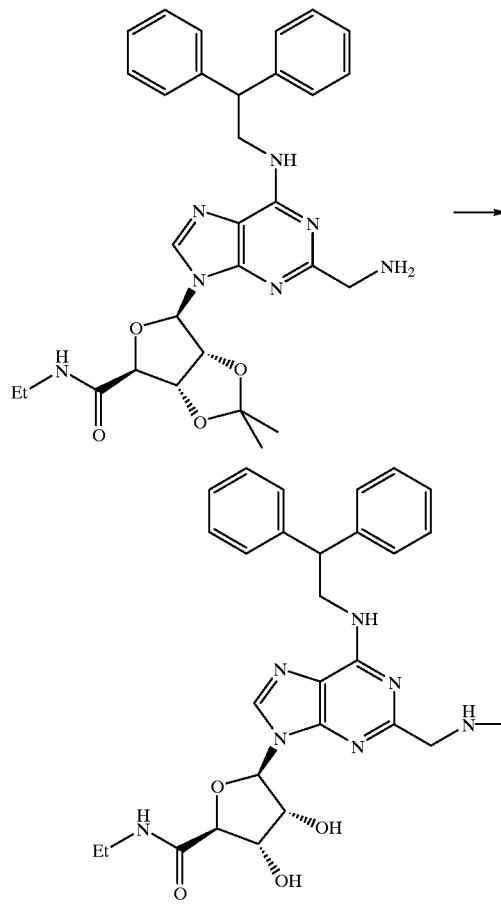

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of 2-propanesulphonyl chloride (40 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1 M, 1 ml) and heated at 60° C. for 4 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether, diluted with pentane, filtered and dried to afford the title compound as a solid (28 mg).

$^1$H-NMR (CDCl$_3$+1 drop DMSO-d$_6$) δ: 7.79 (1H, br s), 7.13–7.38(10H, m), 5.90 (2H, m), 5.64 (1H, t), 4.78 (2H, m), 4.70 (1H, br m), 4.52 (1H, m), 4.31 (6H, m), 3.38 (1H. m), 3.20 (2H, m), 1.37 (6H, d), 1.06 (3H, t).

MS: 623 (M$^+$)

EXAMPLE 4

(2S,3S,4R,5R)-5-(6-[(2,2-Diphenylethyl)amino]-2-{[(phenylsulfonyl)amino]methyl}-9H-purin-9-yl)-N-ethyl-3,4-dihydroxytetrahydro-2-furancarboxamide

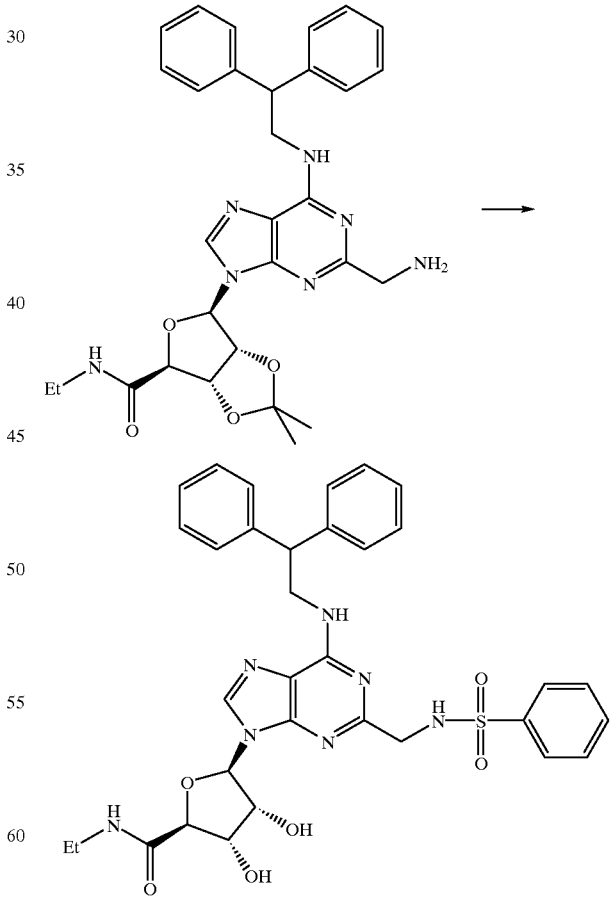

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of benzenesulphonyl chloride (50 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1M, 1 ml) and heated at 60° C. for 8 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether/pentane, filtered and dried to afford the title compound as a solid (85 mg).

$^1$H-NMR (CDCl$_3$+1 drop DMSO-d$_6$) δ: 7.81 (2H, d), 7.76 (1H, br s), 7.12–7.44 (13H, m), 6.10 (1H, t), 5.83 (2H, m), 5.00 (1H, br m), 4.69 (1H, m), 4.61 (1H, br m), 4.53 (1H, m), 4.45 (1H, d), 4.32 (1H, m), 4.20 (4H, m), 3.35 (1H, m), 3.18 (1H, m), 1.04 (3H, t).

Analysis:Found C, 59.84; H, 5.37; N, 14.68%; C$_{33}$H$_{35}$N$_7$O$_6$S. 0.25H$_2$O requires C, 59.85; H, 5.40; N, 14.80%.

EXAMPLE 5

(2S,3S,4R,5R)-5-{2-{[([1,1'-Biphenyl]-4-ylsulfonyl) amino]methyl}-6-[(2,2diphenylethyl)amino]-9H-purin-9-yl}-N-ethyl-3,4-dihydroxytetrahydro-2-furancarboxamide

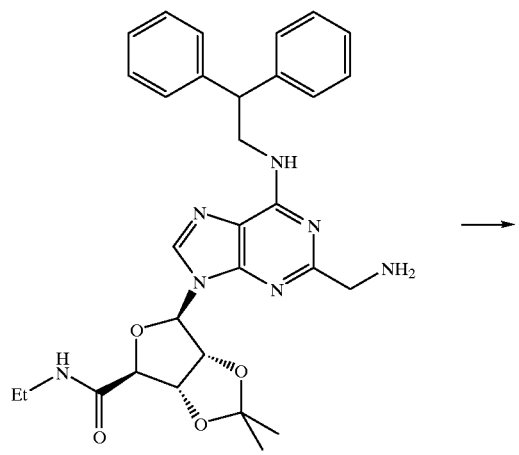

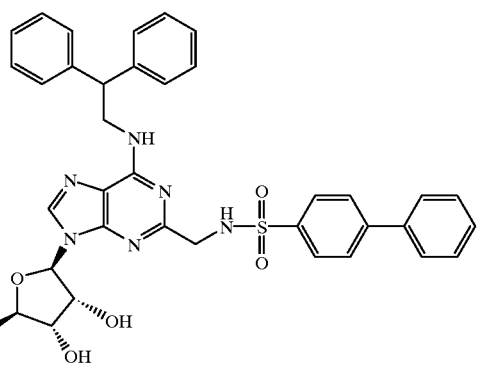

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-][1,3]dioxole4-carboxamide (Preparation 10) (140 mg, 0.25 mmol) and triethylamine (0.05 ml, 0.36 mmol) in anhydrous dichloromethane (1 ml) was treated with a solution of [1,1'-biphenyl]-4-sulfonyl chloride (*J. Pharm. Sci.*, 1964, 53, 73) (71 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1M, 1 ml) and heated at 60° C. for 15 hours. The solvent was removed under reduced pressure and the residue was azeotroped with ethanol (×2). The residue was then purified by column chromatography on silica gel eluting with a gradient system of dichloromethane: methanol (95:5 by volume) gradually changing to dichloromethane:methanol (90:10 by volume) to give a solid which was triturated with diethyl ether, diluted with pentane, filtered and dried to afford the title compound as a solid (110 mg).

$^1$H-NMR (CDCl$_3$+1 drop DMSO-d$_6$) δ: 7.83 (2H, d), 7.74 (1H, br s), 7.13–7.59 (17H, m), 6.18 (1H, t), 5.84 (2H, m), 5.02 (1H, br m), 4.72 (1H, m), 4.58 (1H, br m), 4.48 (2H, m), 4.20 (4H, m), 3.35 (1H, m), 3.20 (1H, m), 1.05 (3H, t).

Analysis:Found C, 63.55; H, 5.38; N, 13.12%; C$_{39}$H$_{39}$N$_7$O$_6$S requires C, 63.83; H, 5.36; N, 13.36%.

EXAMPLE 6

(2S,3S,4R,5R)-5-(6-[(2,2-Diphenylethyl)amino]-2-{[(1-naphthylsulfonyl)amino]methyl}-9H-purin-9-yl)-/N-ethyl-3,4-dihydroxytetrahydro-2-furancarboxamide

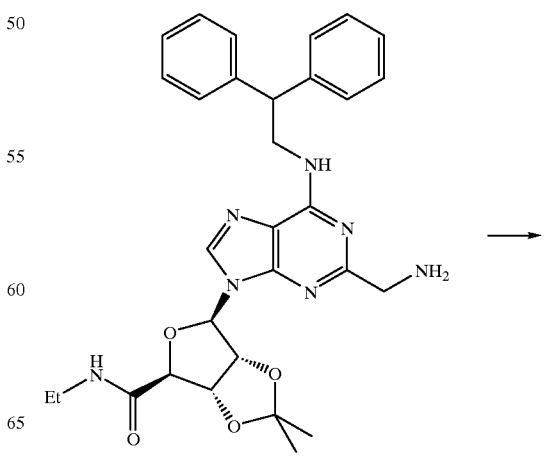

-continued

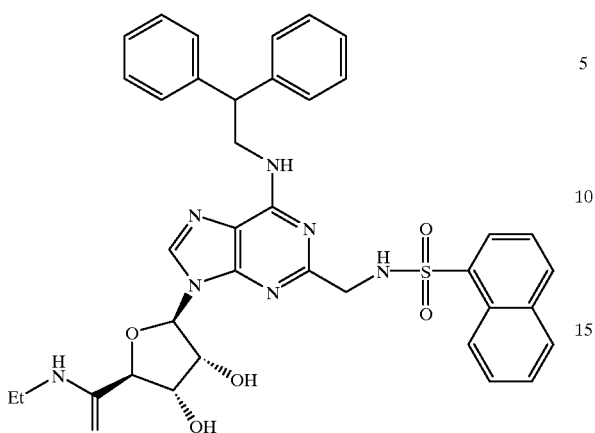

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of 1-naphthalenesulfonyl chloride (63 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1 M, 1 ml) and heated at 60° C. for 5.5 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether, washed with pentane and dried to afford the title compound as a solid (98 mg).

$^1$H-NMR (CDCl$_3$+1 drop DMSO-d$_6$) δ: 8.65 (1H, d), 8.22 (1H, d), 7.93 (1H, d), 7.81 (1H, d), 7.72 (1H, s), 7.15–7.53 (13H, m), 6.28 (1H, t), 5.78 (1H, d), 5.72 (1H, br m), 4.91 (1H, m), 4.62 (2H, m), 4.50 (1H, m), 4.30 (2H, m), 4.08 (4H m), 3.35 (1H, m), 3.17 (1H, m), 1.00 (3H, t).

Analysis:Found C, 62.58; H, 5.29; N, 13.58%; C$_{37}$H$_{37}$N$_7$O$_6$S requires C, 62.79; H, 5.27; N, 13.85%.

EXAMPLE 7
(2S,3S,4R,5 R)-5-(6-[(2,2-Diphenylethyl)amino]-2-{[(2-naphthylsulfonyl)amino]methyl}-9H-purin-9-yl)-N-ethyl-3,4-dihydroxytetrahydro-2-furancarboxamide

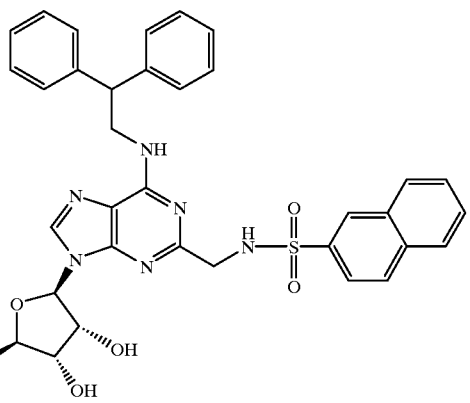

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of 2-naphthalenesulfonyl chloride (63 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1M, 1 ml) and heated at 60° C. for 15 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether, diluted with pentane, filtered and dried to afford the title compound as a solid (88 mg).

$^1$H-NMR (CDCl$_3$+1 drop DMSO-d$_6$) δ: 8.34 (1H, s), 7.79 (4H, m), 7.67 (1H, br s), 7.52 (2H, m), 7.12–7.39 (1 0H, m), 6.20 (1H, t), 5.79 (1H, d), 5.73 (1H, br s), 4.99 (1H, m), 4.63 (1H, m), 4.56 (1H, m), 4.47 (2H, m), 4.17 (5H, m), 3.34 (3.34 (1H, m), 3.16 (1H, m), 0.99 (3H, t).

Analysis:Found C, 62.43; H, 5.28; N, 13.64%; C$_{37}$H$_{37}$N$_7$O$_6$S requires C, 62.79; H, 5.27; N, 13.85%.

EXAMPLE 8

(2S,3S,4R,5R)5-(6-[(2,2-Diphenylethyl)amino]-2-{[(methylsulfonyl)amino]methyl}-9H-purin-9-yl)-N-ethyl-3,4-dihydroxytetrahydro-2-furancarboxamide

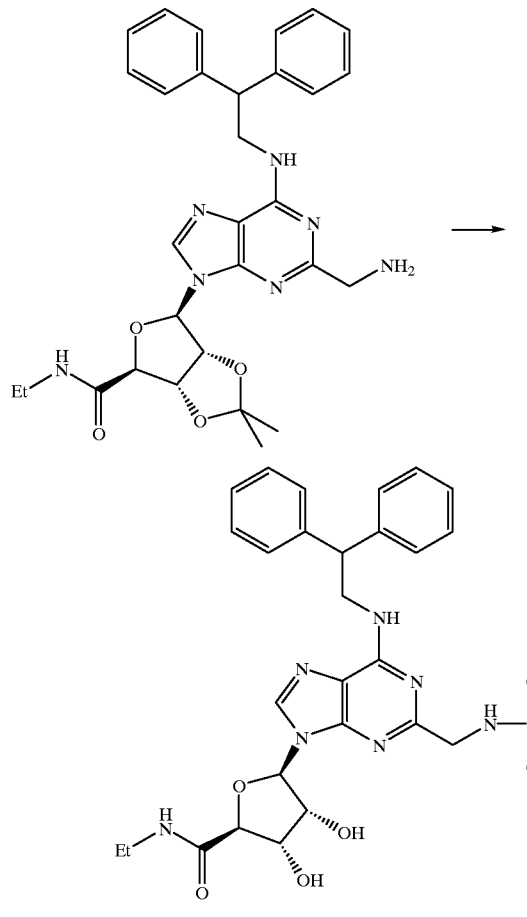

A solution of (3aS,4S,6R,6aR)-6-{2-(aminomethyl)-6-[(2,2-diphenylethyl)amino]-9H-purin-9-yl}-N-ethyl-2,2-dimethyltetrahydrofuro[3,4-d][1,3]dioxole-4-carboxamide (Preparation 10) (140 mg, 0.25 mmol) and triethylamine (0.05 ml, 0.36 mmol) in anhydrous dichloromethane (1 ml) was treated with a solution of methanesulfonyl chloride (32 mg, 0.28 mmol) in anhydrous dichloromethane (1 ml). The mixture was stirred at room temperature for 18 hours during which time the solvent was allowed to evaporate off freely. The residue was dissolved in ethanol (1 ml), treated with hydrochloric acid (1M, 1 ml) and heated at 60° C. for 4 hours. The solvent was removed under reduced pressure and the residue was azeotroped with ethanol (×2). The residue was then purified by column chromatography on silica gel eluting with a gradient system of dichloromethane:methanol (95:5 by volume) gradually changing to dichloromethane:methanol (90:10 by volume) to give a solid which was triturated with diethyl ether, washed with pentane and dried to afford the title compound as a solid (80 mg).

$^1$H-NMR (CDCl$_3$+1 drop DMSO-d$_6$) δ: 7.81 (1H, br s), 7.13–7.37 (10H, m), 5.90 (3H, m), 4.94 (1H, m), 4.75 (1H, m), 4.65 (1H, m), 4.50 (2H, m), 4.32 (4H, m), 3.38 (1H, m), 3.22 (1H, m), 2.90 (3H, s), 1.06 (3H, t).

MS: 596 (MH$^+$)

EXAMPLE 9

(2S,3S,4R,5R)5-(6-[(2,2-Diphenylethyl)amino]-2-{[(isobutylsullonyl)amino]methyl}-9purin-9-yl)-N-ethyl-3,4-dihydroxytetrahydro-2-furancarboxamide

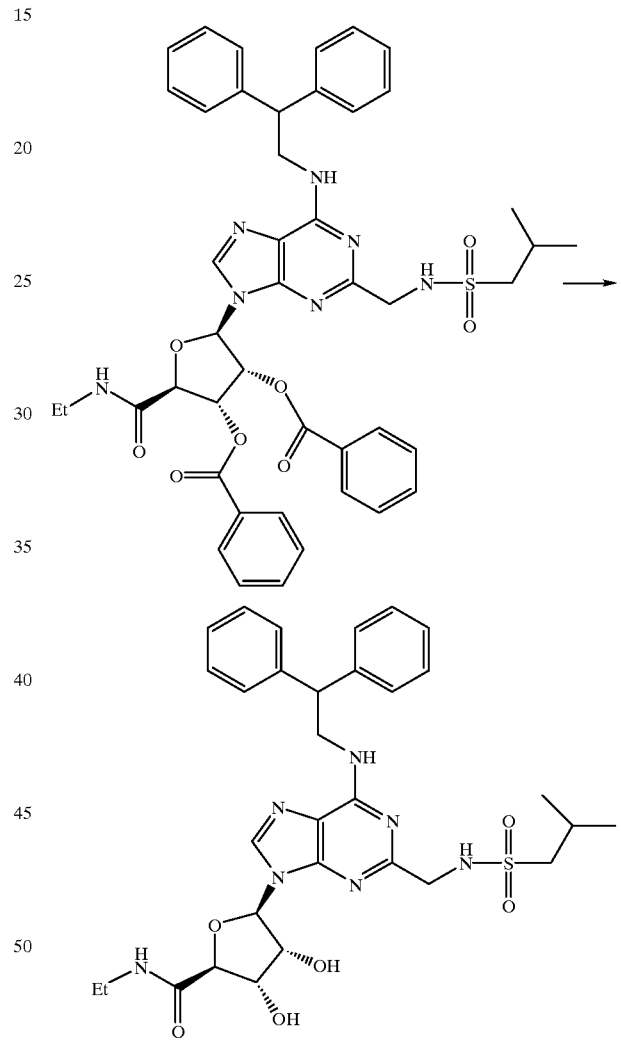

A solution of (2R, 3R, 4S, 5S)-4-(benzoyloxy)-2-(6-[(2, 2-diphenylethyl)amino]-2-25 {[(isobutylsulfonyl)amino] methyl}-9H-purin-9-yl)-5-[(ethylamino)carbonyl] tetrahydro-3-furanyl benzoate (Preparation 14) (290 mg, 0.34 mmol) in methanol (10 ml) was treated with potassium carbonate (190 mg, 1.37 mmol). The mixture was stirred at room temperature for 30 minutes after which time the mixture was filtered and the solvent was removed from the filtrate under reduced pressure. The residue was partitioned between dichloromethane and water. The organic phase was separated, washed with brine, dried over anhydrous magnesium sulphate, filtered and evaporated under reduced pressure. The residue was purified by column chromatography on silica gel eluting with dichloromethane:methanol (95:5 by volume) to afford the title compound as a white solid (170 mg).

$^{1}$H-NMR (DMSO-d$_{6}$) δ: 8.42 (1H, s), 8.25 (1H, m), 7.90 (1H, br m), 7.49 (1H, br m), 7.40 (4H, d), 7.29 (4H, dd), 7.18 (2H, dd), 6.00 (1H, m), 5.67 (1H, m), 5.52 (1H, m), 4.64 (2H, m), 4.13–4.35 (5H, m), 3.20 (2H, m), 2.97 (2H, d), 2.12 (1H, m), 1.06 (3H, t), 0.94 (6H, d).

Analysis:Found C, 57.53; H, 6.11; N, 14.94%; C$_{31}$H$_{39}$N$_{7}$O$_{6}$S. 0.5H$_{2}$O requires C, 57.57; H, 6.23; N, 15.16%.

EXAMPLE 10

(2S,3S,4R,5R)-N-Ethyl-3,4-dihydroxy-5-{2-{[(isobutylsulfonyl)amino]methyl}-6-[(4-methoxybenzyl)amino]-9H-purin-9-yl}tetrahydro-2-furancarboxamide

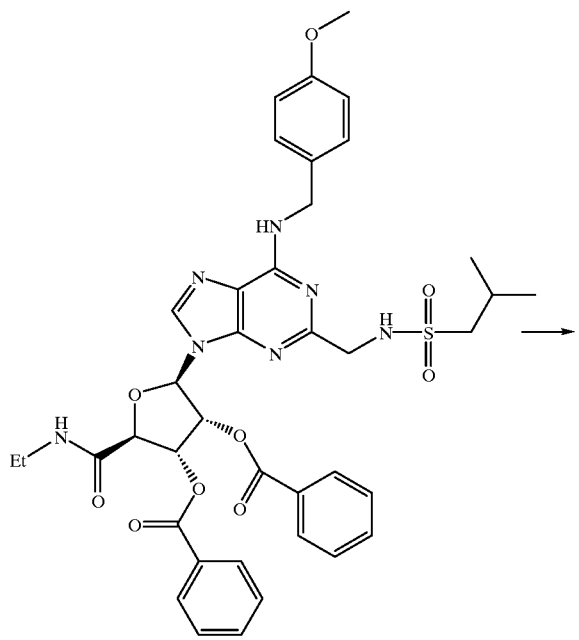

A solution of (2R,3R,4S,5S)-4-(benzoyloxy)-5-[(ethylamino)carbonyl]-2-{2-{[(isobutylsulfonyl)amino]methyl}-6-[(4-methoxybenzyl)amino]-9H-purin-9-yl}tetrahydro-3-furanyl benzoate (Preparation 22) (40 mg, 0.05 mmol) in methanol (2 ml) was treated with potassium carbonate (28 mg, 0.20 mmol). The mixture was stirred at room temperature for 20 minutes after which time a precipitate had formed. Dichloromethane (10 ml) was added to the mixture to dissolve the precipitate. The mixture was then filtered and the filtrate was evaporated under reduced pressure. The residue was purified by column chromatography on silica gel eluting with dichloromethane:methanol (95:5 by volume) to afford the title compound as a white solid (21 mg).

$^{1}$H-NMR (DMSO-d$_{6}$) δ: 8.45 (2H, m), 8.26 (1H, m), 7.34 (3H, m), 6.84 (2H, d), 6.00 (1H, d), 5.69 (1H, m), 5.53 (1H, m), 4.65 (2H, m), 4.30 (1H, m), 4.18 (3H m), 3.70 (3H, s), 3.18 (1H, m), 2.85 (1H, m), 2.03 (1H, m), 1.04 (3H, t), 0.89 (6H, d).

EXAMPLE 11

(2S,3S,4R,5R)-5-{6-[(2,2-Diphenylethyl)amino]-2-[({[2-(1-piperidinyl)ethyl]sulfonyl}amino)methyl]-9H-purin-9-yl}-N-ethyl-3,4-dihydroxytetrahydro-2-furancarboxamide

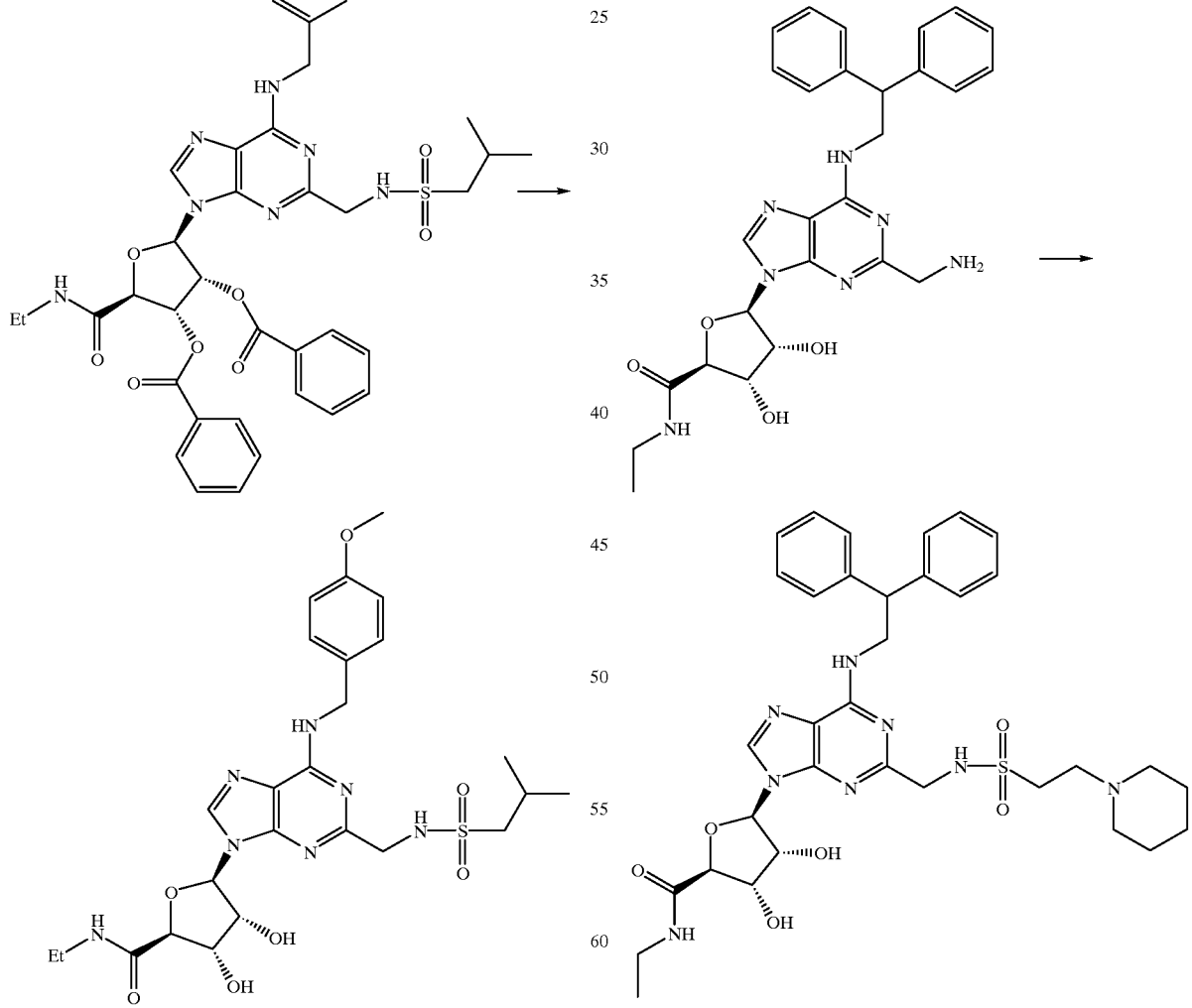

2-Chloroethanesulfonyl chloride (0.12 ml, 1.16 mmol) was added to a solution of (2S,3S,4R,5R)-5-{2-(aminomethyl)-6-[(2,2-diphenylethyl)amino]-9H-purin-9- yl}-N-ethyl- 3,4-dihydroxytetrahydro-2-furancarboxamide (Preparation 27) (600 mg, 1.16 mmol) in a mixture of pyridine (2.5 ml) and acetonitrile (10 ml). The reaction mixture was stirred for 1 hour at room temperature. Piperidine (1.0 ml, 10 mmol) was then added and the reaction mixture was heated under reflux for 16 hours. The reaction mixture was then diluted with ethyl acetate (50 ml) and washed with water (30 ml). The ethyl acetate layer was dried (anhydrous magnesium sulphate) and evaporated under reduced pressure. The residue was purified by column chromatography on silica gel eluting with dichloromethane:methanol:ammonia (95:5:0.5 by volume) increasing in polarity to dichloromethane:methanol:ammonia (90:10:1 by volume). The solvent was removed under reduced pressure and the residue repurified by column chromatography on silica gel eluting with ethyl acetate::methanol:ammonia (95:5:0.5 by volume) increasing in polarity to ethyl acetate:methanol:ammonia (90:10:1 by volume). The solvent was removed under reduced pressure and the residue was repurified by column chromatography on silica gel eluting with ethyl acetate:methanol (95:5 by volume) increasing in polarity to ethyl acetate:methanol (90:10 by volume) then ethyl acetate:methanol:ammonia (90:10:1 by volume). The solvent was removed under reduced pressure to give the title compound (21 mg).

MS: 693 (MH$^+$)

$^1$H-NMR (CD$_3$OD) δ: 8.30 (1H, s), 7.35–7.10 (1 0H, m), 6.35–6.30 (1H, m), 5.85–5.80 (1H, m), 4.55–4.50 (2H, m), 4.30 (2H, br s), 3.90 (2H, br s), 3.45–3.40 (2H, m), 3.30–3.20 (2H, m), 2.80–2.70 (1H, m), 2.65–2.55 (1H, m), 2.35–2.25 (4H, m,), 1.65–1.50 (4H, m), 1.45–1.35 (2H, m), 1.10–1.05 (3H, m).

The following Preparations describe the preparation of certain intermediates used in the preceding Examples.

PREPARATION 1: 2,6-Dichloro-9-tetrahydro-2H-pyran-2-yl-9H-purine

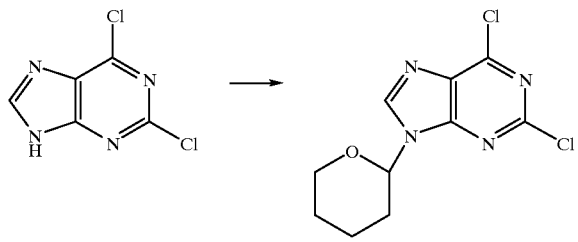

2,6-Dichloro-9H-purine (20 g, 0.11 mol) and 4-toluenesulphonic acid monohydrate (0.2 g) were dissolved in ethyl acetate (300 ml), the mixture was heated to 50° C. and a solution of 2,3-dihydropyran (12.6 ml, 0.14 mol) in ethyl acetate (50 ml) was added slowly over 30 minutes. The reaction mixture was then cooled to room temperature, water (100 ml) was added and the pH of the solution was adjusted to 7 by addition of a saturated aqueous solution of sodium hydrogen carbonate. The organic layer was separated, washed sequentially with water and brine, dried over anhydrous magnesium sulphate, filtered and evaporated under reduced pressure. The residue was azeotroped from pentane (×2) to afford the title compound as a slightly impure white solid (30.9g).

$^1$H-NMR (CDCl$_3$) δ: 8.30 (1H, s), 5.75 (1H, dd), 4.25–4.15 (1H, m), 3.85–3.70(1H, m), 2.20–1.60 (6H, m).

PREPARATION 2: 2-Chloro—S(2,2-diphenylethyl)-9-tetrahydro-2H-pyran-2-yl-9H-purin-6-amine

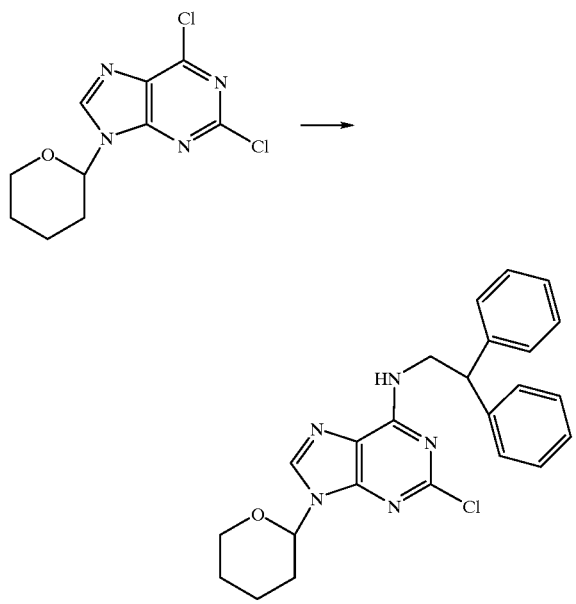

A solution of 2,6-dichloro-9-tetrahydro-2H-pyran-2-yl-9H-purine (Preparation 1) (30.9g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture was heated at reflux for 3 hours. The solvent was removed under reduced pressure and the residue was azeotroped from ethyl acetate. The residue was then purified by column chromatography 10 on silica gel eluting with a gradient system of ethyl acetate:hexane (40:60 by volume) gradually changing to ethyl acetate:hexane (60:40 by volume) to afford the title compound as a foam (49.7 g).

$^1$H-NMR (CDCl$_3$) δ: 7.95–7.75 (1H, br s), 7.35–7.15 (10H, m), 5.80–5.70 (1H, br s), 5.65 (1H, d), 4.35 (1H, m), 4.304.18 (1H, br s), 4.10 (1H, d), 3.70 (1H, t), 2.05–1.95 (2H, m), 1.95–1.80 (1H, m), 1.80–1.55 (3H, m).

PREPARATION 3: N(2,2-Diphenylethyl)-2-(methylsulfanyl)-9-tetrahydro-2H-pyran-2-yl-9H-purin-6-amine

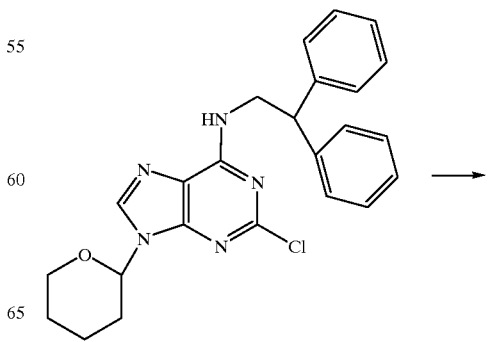

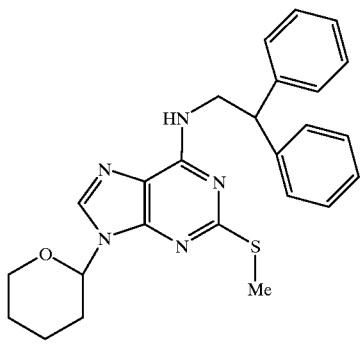

A solution of 2-chloro-N-(2,2-diphenylethyl)-9-tetrahydro-2H-pyran-2-yl-9H-purin-6-amine (Preparation 2) (49.7g, 0.11 mol) in dry N,N-dimethylformamide (200 ml) was treated with sodium thiomethoxide (10 g, 0.14 mol) and the resulting mixture was heated under an atmosphere of nitrogen at 100° C. for 90 minutes. The mixture was then stirred at room temperature for 72 hours and then reheated at 100° C. for a further 2 hours. The reaction mixture was then cooled and diluted with water (1000 ml). A suspension was formed which was extracted into diethyl ether (×2). The combined organic layers were washed sequentially with water and brine, dried over anhydrous magnesium sulphate, filtered and evaporated under reduced pressure. The residue was azeotroped from diethyl ether followed by pentane to afford the title compound as a foam (48.9 g).

$^1$H-NMR (CDCl$_3$) δ8 7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

PREPARATION 4; N(2,2-Diphenylethyl)-2-(methylsulfonyl)-9-tetrahydro-2H-pyran-2-yl-9H-purin-6amine

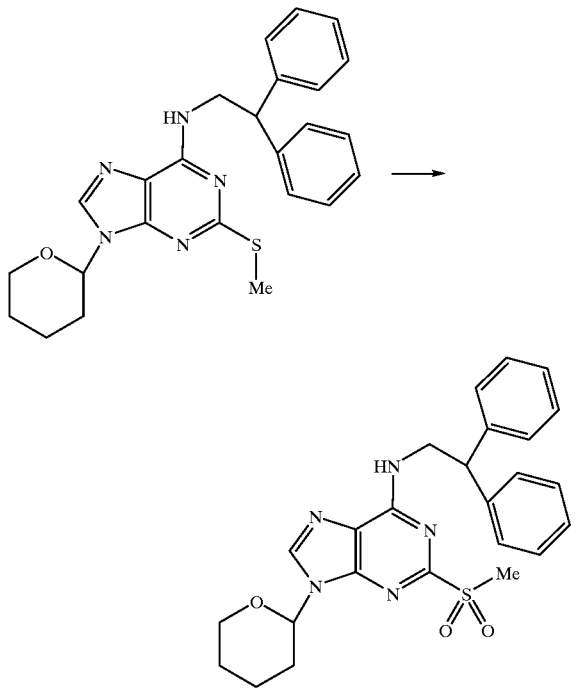

A solution of Oxone (trade mark) (potassium peroxymonosulphate) (44 g, 71.7 mmol) in water (200 ml) was added drop wise over 2 hours to a solution of N-(2,2-diphenylethyl)-2-(methylsulfanyl)-9-tetrahydro-2H-pyran-2-yl-9H-purin-6-amine (Preparation 3) (25 g, 56.2 mmol) and sodium hydrogen carbonate (20 g, 238 mmol) in acetone (1000 ml) and water (250 ml). The resultant mixture was stirred at room temperature for 24 hours and filtered and the residue was washed with acetone. The acetone was removed from the filtrate under reduced pressure and the resulting aqueous residue was extracted with ethyl acetate and then dichloromethane. The combined organic layers were washed with brine, dried with anhydrous magnesium sulphate, filtered and evaporated under reduced pressure. The residue was triturated with diethyl ether, filtered, washed with diethyl ether and pentane and then dried to afford the title compound as a white solid (20.32 g).

$^1$H-NMR (CDCl$_3$) δ: 8.00 (1H, s), 7.35–7.15 (10H, m), 6.05–5.95 (1H, br s), 5.75 (1H, d), 4.40–4.35 (1H, m), 4.35–4.20 (2H, brs), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

PREPARATION 5: 6-[(2,2-Diphenylethyl)amino]-9-tetrahydro-2Spyran-2-yl-9H-purine-2-carbonitrile

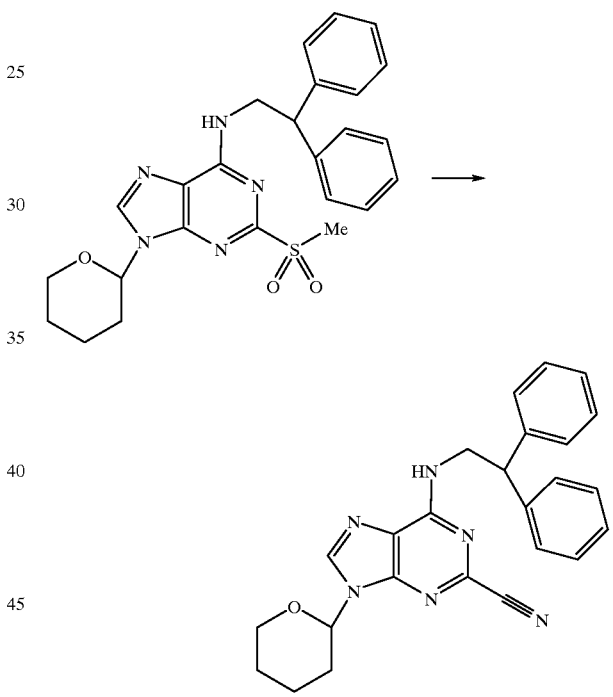

A solution of N(2,2-diphenylethyl)-2-(methylsulfonyl)-9-tetrahydro-2H-pyran-2-yl-9H-purin-6-amine (Preparation 4) (20.1 g, 42.1 mmol) in dry N,N-dimethylformamide (100 ml) was treated with potassium cyanide (5.5 g, 84.6 mmol) and the mixture was heated at 120° C. for 24 hours under a nitrogen atmosphere. The mixture was then cooled to room temperature, diluted with 20 water (1000 ml) and stirred for a further 1 hour. The resultant solid was slowly filtered and washed several times with water. The solid was dissolved in dichloromethane and the resulting solution washed with water, dried with anhydrous magnesium sulphate, filtered and evaporated under reduced pressure. The residue was azeotroped from diethyl ether twice to afford the title compound as an oil (17 g).

$^1$H-NMR (CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

PREPARATION 6: 6-[(2,2-Diphenylethyl)amino]-9H-purine-2-carbonitrile

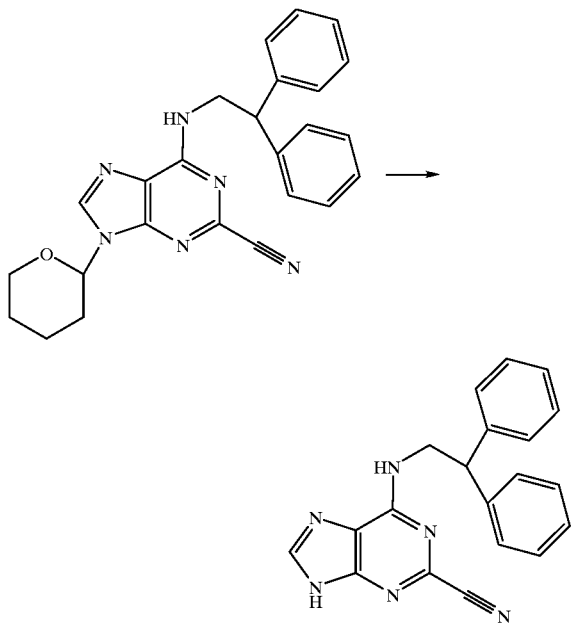

A solution of 6-[(2,2-diphenylethyl)amino]-9-tetrahydro-2H-pyran-2-yl-9H-purine-2-carbonitrile (Preparation 5) (17.0 g, 40.1 mmol) in ethanol (850 ml) was treated with hydrochloric acid (2N, 50 ml) and the mixture was stirred at room temperature for 24 hours. The solvent was removed under reduced pressure and the residue was azeotroped from ethanol twice. The residue was triturated with diethyl ether and the resulting solid was filtered, washed with diethyl ether and pentane and dried to afford the title compound as a solid (14.3 g).

MS: 341 (MH$^+$)

$^1$H-NMR (DMSO-d$_6$) δ: 8.30 (1H, s), 8.05–8.20 (1H, br s), 7.10–7.40 (10H, m), 4.40–4.60 (1.4H, m), 4.00–4.20 (1.6H, m).

PREPARATION 7: (2S,3S,4R,5R)-4-(Benzoyloxy)-5-{2-cyano-6-[(2,2-diphenylethyl)amino]-9H-purin-9-yl}-2-[(ethylamino)carbonyl]tetrahydro-3-furanyl benzoate

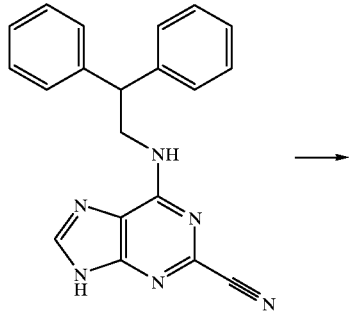

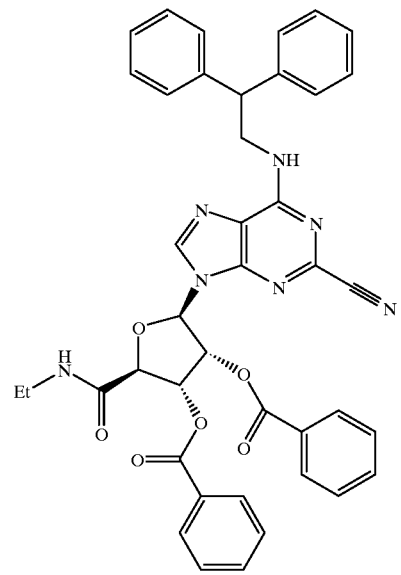

A mixture of 6-[(2,2-diphenylethyl)amino]-9H-purine-2-carbonitrile (Preparation 6) (5.00 g, 14.7 mmol), (2S,3R,4R)-5-(acetyloxy)-4-(benzoyloxy)-2-[(ethylamino)carbonyl]tetrahydro3-furanyl benzoate (Preparation 26) (6.50 g, 14.7 mmol) and iodine (0.38 g, 15.0 mmol) was heated at 150° C. under reduced pressure for 2.5 hours and then left to stand at room temperature for 18 hours. The residue was purified by column chromatography on silica gel eluting with a gradient system of ethyl acetate:pentane (40:60 by volume) gradually changing to pure ethyl acetate to afford the title compound as a foam (4.95 g).

$^1$H-NMR (CDCl$_3$) δ: 8.12 (3H, m), 7.79 (3H, m), 7.63 (1H, m), 7.50 (3H, m), 7.16–7.38 (11H, m), 6.35 (2H, m), 6.10 (1H, t), 6.03 (1H, d), 4.94 (1H, m), 4.35 (3H, m), 3.57 (2H, m), 1.30 (3H, t).

PREPARATION 8: (2S,3S,4R,5R)-5-{2-Cyano6-[(2,2-diphenylethyl)amino]-9H-purin-9-yl}-N-ethyl-3,4-dihydroxytetrahydro-2-furancarboxamide

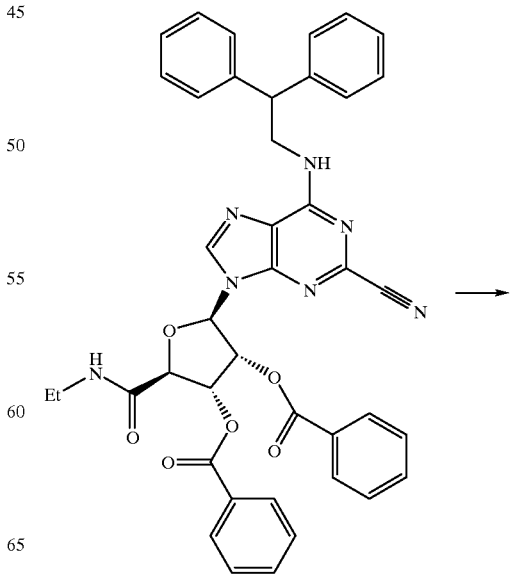

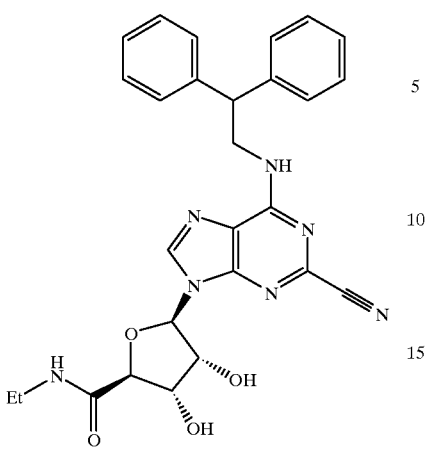

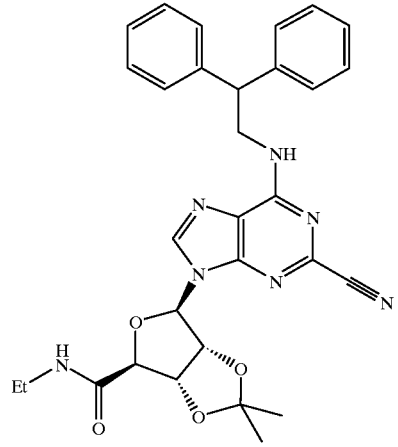

A solution of (2S,3S,4R,5R)-4-(benzoyloxy)-5-{2-cyano-6-[(2,2-diphenylethyl)amino]-9H-purin-9-yl}-2-[(ethylamino)carbonyl]tetrahydro-3-furanyl benzoate (Preparation 7) (4.75 g, 6.59 mmol) in ethanol (200 ml) was saturated with ammonia gas and stirred at room temperature for 18 hours. The solvent was removed under reduced pressure and the residue was purified by column chromatography on silica gel eluting with a gradient system of dichloromethane:methanol (95:5 by volume) gradually changing to dichloromethane:methanol (90:10 by volume) to afford the title compound as a solid (2.80 g).

$^1$H-NMR (DMSO-d$_6$) δ: 8.65 (1H, s), 8.54 (1H, br t), 8.18 (1H, br m), 7.13–7.42 (10H, m), 5.98 (1H, m), 5.65 (1H, m), 5.57 (1H, m), 4.59 (2H, m), 4.32 (1H, m), 4.08–4.28 (3H, m), 3.20 (2H, m), 1.05 (3H, t).

PREPARATION 9: (3aS,4S,6R,6a)-6-{2-Cyano-6-[(2,2-diphenylethyl)amino]-9H-purin-9-yl}-ethyl-2,2-dimethyltetrahydrofuro[3,4-d][1,3]dioxole-4-carboxamide A suspension of (2S,3S,4R,5R)-5-{2-cyano-6-[(2,2-diphenylethyl)amino]-9H-purin-9-yl}-N-ethyl-3,4-dihydroxytetrahydro-2-furancarboxamide (Preparation 8) (2.80 g, 5.46 mmol) and 2,2-dimethoxypropane (8.93 g, 85.87 mmol) in acetone (70 ml) was treated with 10-camphorsulphonic acid (1.33 g, 5.73 mmol). The resulting solution was stirred at room temperature for 3 hours. The solvent was removed under reduced pressure and the residue was purified by column chromatography on silica gel eluting with a gradient system of diethyl ether:dichloromethane::ethyl acetate (66:44:0 by volume) gradually changing to (100:0:0 by volume) and then to (0:0:100 by volume). The residue was then dissolved in a mixture of diethyl ether and ethyl acetate and the resulting solution was washed sequentially with saturated aqueous sodium hydrogen carbonate, water and brine. The organic phase was separated, dried over anhydrous magnesium sulphate, filtered and evaporated under reduced pressure to afford the title compound as a solid (2.85 g).

MS: 554 (MH$^+$)

$^1$H-NMR (CDCl$_3$) δ: 7.85 (1H, s), 7.20–7.40 (10H, m), 6.82 (1H, m), 6.00 (2H, m), 5.26 (2H, m), 4.75 (1H, m), 4.33 (3H, m), 3.28 (2H, m), 1.63 (3H, s), 1.39 (3H, s), 1.02 (3H, t).

PREPARATION 10: (3aS,4S,6R,6aR)-6-{2-(Aminomethyl) 6-[(2,2-diphenylethyl)amino]-9H-purin-9-yl}-Methyl-2,2-dimethyltetrahydrofuro[3,4-d][1,3]dioxole-4-carboxamide

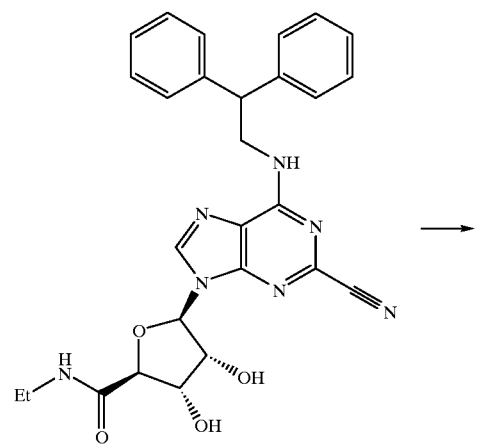 →

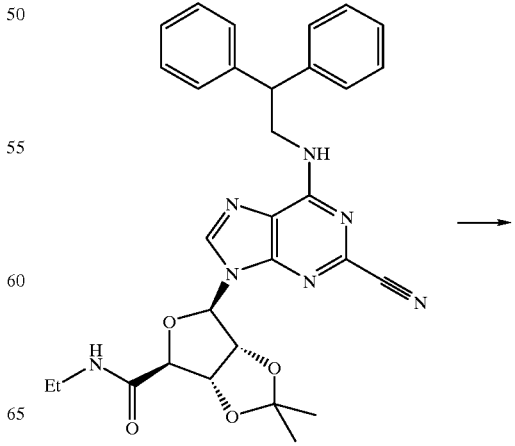 →

37

-continued

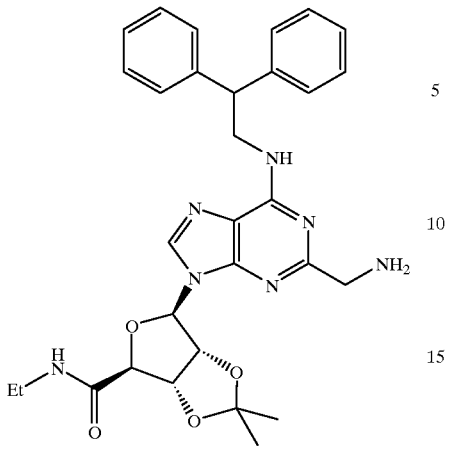

A solution of (3aS,4S,6R,6aR)-6-{2-cyano-6-[(2,2-diphenylethyl)amino]-9H-purin-9-yl}-N-ethyl-2,2-dimethyltetrahydrofuro[3,4-d][1,3]dioxole4-carboxamide (Preparation 9) (2.70 g, 4.88 mmol) in ethanol (150 ml) was saturated with ammonia gas, treated with 5% wlw palladium on charcoal (1.00 g), pressurised to 1034 kPa (150 psi) with hydrogen in a sealed vessel and stirred at room temperature for 18 hours. TLC analysis indicated some starting material remaining and so further 5% wlw palladium on charcoal (1.00 g) was added and the solution was again pressurised to 1034 kPa (150 psi) with hydrogen in a sealed vessel and stirred at room temperature for 24 hours. The mixture was then filtered through a pad of Arbocel (trade mark) and the filtrate was evaporated under reduced pressure. The residue was purified by column chromatography on silica gel eluting with a gradient system of dichloromethane:methanol (95:5 by volume) gradually changing to dichloromethane:methanol (90:10 by volume) to afford the title compound as a foam (2.50 g).

MS: 558 (MH+)

$^1$H-NMR (CDCl$_3$) δ: 7.71 (1H, brs), 7.14–7.40 (10H, m), 6.08 (1H, m), 6.00 (1H t), 5.66 (2H, m), 5.47 (1H, d), 4.66 (1H, s), 4.33 (3H, m), 3.95 (2H, m), 2.98 (1H, m), 2.71 (1H, m), 2.40 (2H, br m), 1.62 (3H, s), 1.41 (3H, s), 0.63 (3H, t).

PREPARATION 11: N-[2-(Aminomethyl)-9-tetrahydro-2H-pyran-2-yl-9H-purin-6-yl]-N-(2,2-diphenylethyl)amine

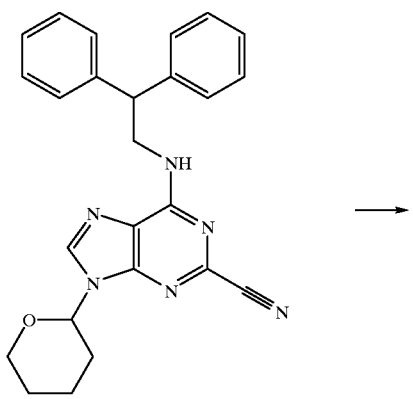

38

-continued

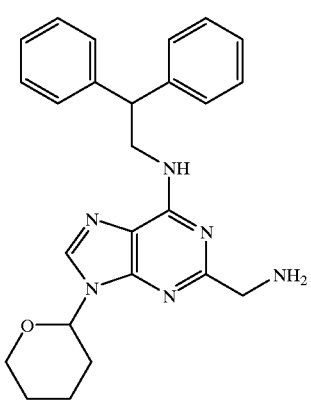

A solution of 6-[(2,2-diphenylethyl)amino]-9-tetrahydro2H-pyran-2-yl-9H-purine-2-carbonitrile (Preparation 5) (5.70 g, 13.1 8 mmol) in ethanol (200 ml) was saturated with ammonia gas, treated with Pearlmann's catalyst (1.00 g), pressurised to 414 kPa (60 psi) with hydrogen in a sealed vessel and stirred at room temperature for 30 hours. The mixture was filtered through a pad of Arbocel (trade mark) and the solvent was removed under reduced pressure. The residue was azeotroped from dichloromethane (×2) and then purified by column chromatography on silica gel eluting with dichloromethane:methanol (95:5 by volume) gradually changing to dichloromethane:methanol: 0.88 ammonia (90:10:0.5 by volume) to afford the title compound (4.34 g).

MS: 429 (MH+)

$^1$H-NMR (CDCl$_3$) δ: 7.84 (1H, s), 7.14–7.36 (10H, m), 5.70 (1H, d), 5.60 (1H, br s), 4.20–4.42 (3H, m), 4.14 (1H, d), 3.95 (2H, s), 3.78 (1H, t), 1.90–2.20 (5H, m), 1.50–1.88 (3H, m).

PREPARATION 12: ({6-[(2,2-Diphenylethyl)amino]-9-tetrahydro-2H pyran-2-yl-9H-purin-2-yl}methyl)-2-methyl-1-propanesulfonamide

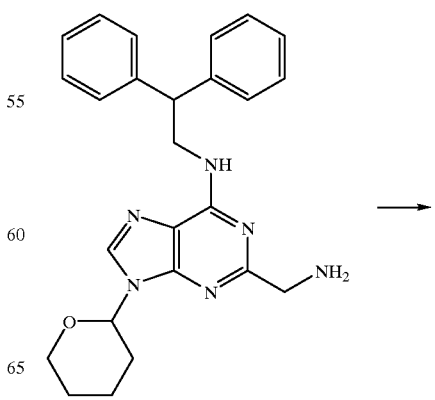

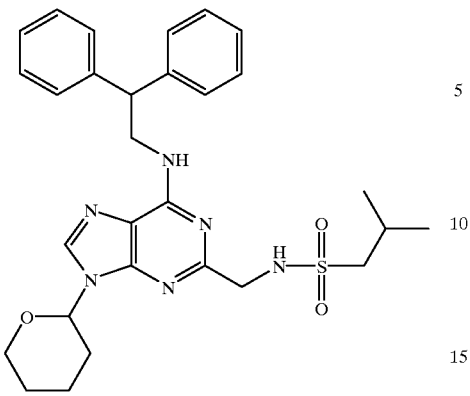

A solution of M[2-(aminomethyl)-9-tetrahydro-2H-pyran-2-yl-9H-purin-6-yl]-N-(2,2-diphenylethyl)amine (Preparation 11) (3.70 g, 8.63 mmol) and triethylamine (2.20 g, 21.78 mmol) in dry dichloromethane (20 ml) was treated with 2-methyl-1-propanesulfonyl chloride (*J. Prakt. Chem.*, 1979, 321, 107–111) (1.48 g, 9.46 mmol) and the mixture was stirred at room temperature for 18 hours. TLC analysis indicated some starting material still remained and so further 2-methyl-1-propanesulfonyl chloride (0.2 g, 1.28 mmol) was added and the mixture was stirred at room temperature for 1 hour. The solvent was removed under reduced pressure and the residue was purified by column chromatography on silica gel eluting with dichloromethane:methanol (98:2 by volume) to afford the title compound as a foam (4.4 g).

MS: 549 (MH$^+$)

$^1$H-NMR (CDCl$_3$) δ: 7.86 (1H, s), 7.16–7.36 (10H, m), 5.74 (1H, br s), 5.64 (1H, d), 5.57 (1H, t), 4.18–4.46 (5H, m), 4.14 (1H, d), 3.77 (1H, t), 2.92 (2H, d), 2.228 (1H, m) 1.92–2.10 (3H, m), 1.58–1.88 (3H, m), 1.03 (6H, d).

PREPARATION 13: N({6-[(2,2-Diphenylethyl)amino]-9H-purin-2-yl}methyl)-methyl-1-propanesulfonamide hydrochloride A solution of N({6-[(2,2-diphenylethyl)amino]-9-tetrahydro-2H-pyran-2-yl-9H-purin-2-yl}methyl)-2-methyl-1-propanesulfonamide (Preparation 12) (4.30 g, 7.84 mmol) in ethanol (100 ml) was heated to 37° C. and then treated with hydrochloric acid (2N, 15 ml). The mixture was left to stand at room temperature for 18 hours, after which time a crystalline precipitate was filtered off, washed with ethanol (10 ml) and dried to afford the title compound as a solid (3.0 g).

$^1$H-NMR (DMSO-d$_6$) δ: 8.48 (1H, br s), 7.75 (1H, br s), 7.37 (4H, d), 7.27 (4H, dd), 7.16 (2H, dd), 4.56 (1H, t), 4.20–4.40 (4H, m), 2.95 (2H, d), 2.10 (1H, m), 0.95(6H, d).

PREPARATION 14: (2R,3R, 4S, 5s)-4-(Benzoyloxy)-2-(6-[(2,2-diphenylethyl)amino]-2-{[(isobutylsulfonyl)amino]methyl}-9H-purin-9-yl)-5-[(ethylamino)carbonyl]tetrahydro-3-furanyl benzoate

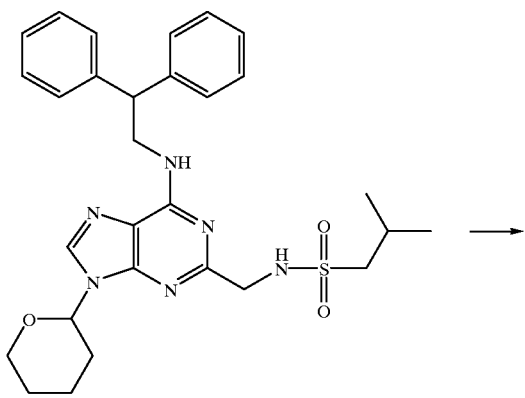

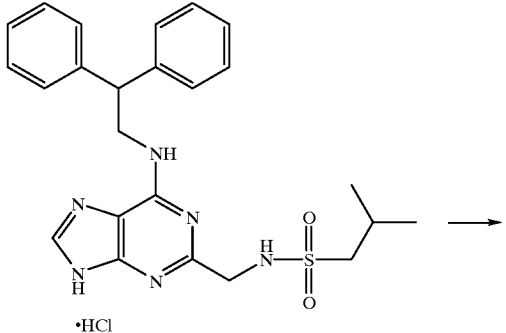

-continued

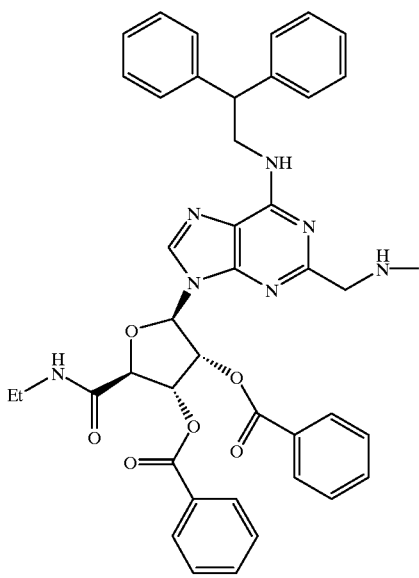

A suspension of N({6-[(2,2-diphenylethyl)amino]-9H-purin-2-yl}methyl)-2-methyl-1-propanesulfonamide hydrochloride (Preparation 13) (0.25 g, 0.50 mmol) in 1,1,1,3,3,3-hexamethyldisilazane (10 ml) was heated under reflux under a nitrogen atmosphere for 90 minutes until a solution was obtained. The solution was allowed to cool to room temperature and the solvent was removed under reduced pressure. The residue was azeotroped from dichloromethane and then acetonitrile. The residue was dissolved in acetonitrile (5 ml) and treated with a solution of (2S,3R,4R)-5-(acetyloxy)-4-(benzoyloxy)-2-[(ethylamino)carbonyl]tetrahydro-3-furanyl benzoate (Preparation 26) (0.26 g, 0.59 mmol) in acetonitrile (5 ml) and trimethylsilyl trifluoromethanesulfonate (0.1 ml, 0.59 mmol). The resulting solution was then stirred at room temperature under a nitrogen atmosphere for 18 hours. The mixture was diluted with ethyl acetate (20 ml) and washed with a saturated aqueous solution of sodium hydrogen carbonate. The organic layer was separated, washed with brine, dried over anhydrous magnesium sulphate, filtered and evaporated under reduced pressure. The residue was purified by column chromatography on silica gel eluting with a gradient system of dichloromethane:methanol (99.5:0.5 by volume) gradually changing to dichloromethane:methanol (99:1 by volume) to afford the title compound as a white foam (0.29 g).

MS: 846 (MH$^+$), 868 (MNa$^+$)

$^1$H-NMR (CDCl$_3$) δ: 8.05 (2H, d), 7.94 (1H, br s), 7.84 (2H, d), 7.60 (1H, dd), 7.54 (1H, dd), 7.46 (2H, dd), 7.20–7.40 (11H, m), 7.00 (1H, m), 6.33 (3H, m), 5.92 (1H, m), 5.75 (1H, m), 4.92 (1H, d), 4.20–4.52 (5H, m), 3.47 (1H, m), 3.33 (1H, m), 2.97 (2H, m), 2.29 (1H, m), 1.15 (3H, t), 1.06 (6H, d).

PREPARATION 15: 2-Chloro-N(4-methoxybenzyl)-9-tetrahydro-2H-pyran-2-yl-9H-purin-6-amine

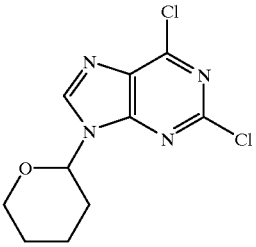 

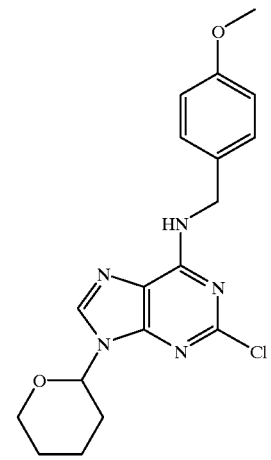

A suspension of 2,6-dichloro-9-tetrahydro-2H-pyran-2-yl-gH-purine (Preparation 1) (30.0 g, 110 mmol) in propan-2-ol (600 ml) was treated with 4-methoxybenzylamine (15.8 ml, 121 mmol) and N,N-diisopropylethylamine (45.6 ml, 264 mmol). The resulting mixture was heated to 60° C. at which point a solution was obtained. During the following 30 minutes a white solid precipitated from the reaction mixture. After cooling the mixture to room temperature, the precipitate was filtered off and washed with propan-2-ol to afford the title compound as a white solid (36.3 g).

MS: 374 (MH$^+$)

$^1$H-NMR (CDCl$_3$) δ: 7.90 (1H, s), 7.28 (2H, d), 6.97 (2H, d), 6.24 (1H, br m), 5.69 (1H, dd), 4.78 (2H, br m), 4.15 (1H, dd), 3.77 (4H, m), 1.40–2.16 (6H, m).

PREPARATION 16: N(4Methoxybenzyl)-2-(methylsulfanyl)-9-tetrahydro-2H-pyran-2-yl-9H-purin-6-amine

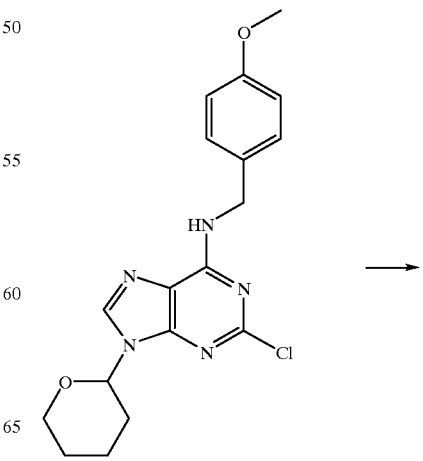

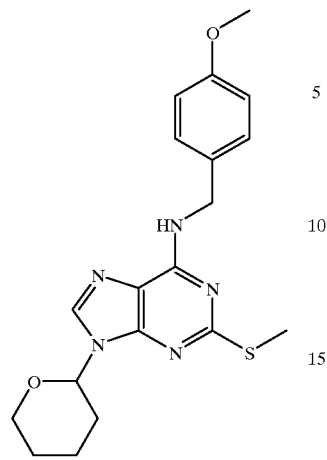

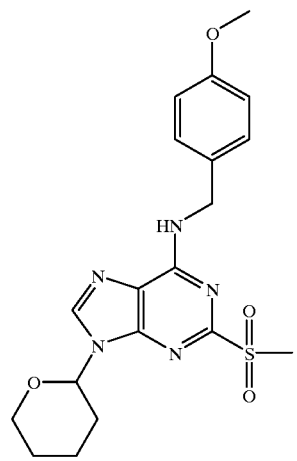

A suspension of 2-chloro-N(4-methoxybenzyl)-9-tetrahydro-2H-pyran-2-yl-9H purin-6-amine (Preparation 15) (37.4 g, 100 mmol) in N,N-dimethylformamide (150 ml) was treated with sodium methanethiolate (8.75 g, 125 mmol) and the mixture was heated at 100° C. under a nitrogen atmosphere for 17 hours. TLC analysis showed that some starting material still remained and so further sodium methanethiolate (3.5 g, 50 mmol) was added and the mixture was heated at 100° C. for 1 hour. The mixture was cooled and the solvent was removed under reduced pressure. The residue was partitioned between dichloromethane and water. The organic phase was separated, washed sequentially with water and brine, dried over anhydrous magnesium sulphate, filtered and evaporated under reduced pressure to afford the title compound as a white solid (40.5 g).

MS: 386 (MH$^+$), 408 (MNa$^+$)

$^1$H-NMR (CDCl$_3$) δ: 7.79 (1H, s), 7.28 (2H, d), 6.85 (2H, d), 6.10 (1H, br m), 5.64 (1H, dd), 4.78 (2H, br m), 4.13 (1H, dd), 3.77 (4H, m), 2.58 (3H, s), 1.60–2.17 (6H, m).

PREPARATION 17: (4-Methoxybenzyl)-2-(methylsulfonyl)-9-tetrahydro-1pyran-2-yl-9H-purin-6-amine A solution of oxone (trade mark) (potassium peroxymonosulphate) (82.93 g, 135 mmol) in water (400 ml) was added dropwise over 1 hour to a stirred suspension of N(4-methoxybenzyl)-2-(methylsulfanyl)-9-tetrahydro-2H-pyran-2-yl-9H-purin-6-amine (Preparation 16) (40 g, 104 mmol) and sodium hydrogen carbonate (32 g, 381 mmol) in mixture of acetone (1000 ml) and water (50 ml). The resulting mixture was stirred at room temperature for 48 hours and filtered and the residue was washed with acetone. The acetone was removed from the filtrate under reduced pressure and the resulting aqueous residue was extracted with dichloromethane. The organic phase was separated, washed with brine, dried over anhydrous magnesium sulphate, filtered and evaporated to afford the title compound as a cream foam (39.28 g).

MS: 418 (MH$^+$), 440 (MNa$^+$)

$^1$H-NMR (CDCl$_3$) δ: 8.07 (1H, s), 7.29 (2H, d), 6.86 (2H, d), 6.51 (1H, br m), 5.78 (1H, dd), 4.78 (2H, br m), 4.16 (1H, dd), 3.80 (4H, m), 3.33 (3H, s), 1.60–2.20 (6H, m).

PREPARATION 18: 6-[(4-Methoxybenzyl)amino]-9-tetrahydro-2H-pyran-2-yl-9Spurine-2-carbonitrile

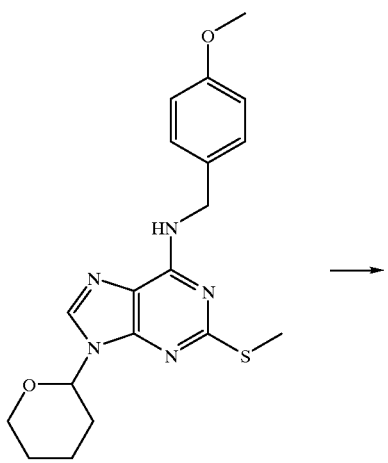 →

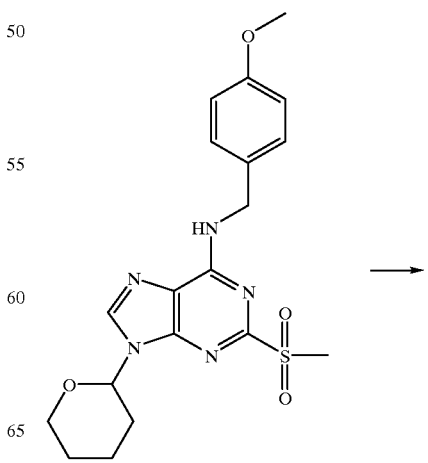 →

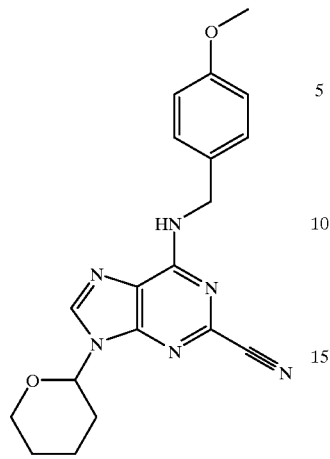

A solution of N-(4-methoxybenzyl)-2-(methylsulfonyl)-9-tetrahydro-2H-pyran-2-yl-9H-purin-6-amine (Preparation 17) (20.0 g, 47.9 mmol) in N,N-dimethylformamide (100 ml) was treated with potassium cyanide (6.24 g, 95.8 mmol) and the resulting mixture was heated at 100° C. under a nitrogen atmosphere for 48 hours. The mixture was then cooled to room temperature, diluted with water (1000 ml) and stirred for 2 hours. The resulting solid was filtered off and washed with water several times. The solid was then dissolved in dichloromethane and washed sequentially with water and brine. The organic layer was separated, dried over anhydrous magnesium sulphate, filtered and evaporated under reduced pressure. The resulting solid was triturated with diethyl ether to afford the title compound as a light brown solid (14.76 g).

MS: 365 (MH$^+$)

$^1$H-NMR (CDCl$_3$) δ: 8.04 (1H, s), 7.27 (2H, d), 6.86 (2H, d), 6.28 (1H, br m), 5.70 (1H, dd), 4.75 (2H, br m), 4.17 (1H, dd), 3.80 (4H, m), 1.60–2.20 (6H, m

PREPARATION 19: 2-(Aminomethyl)-N-(4-methoxybenzyl)-9-tetrahydro-2H-yran-2-yl-9H-purin-6-amine

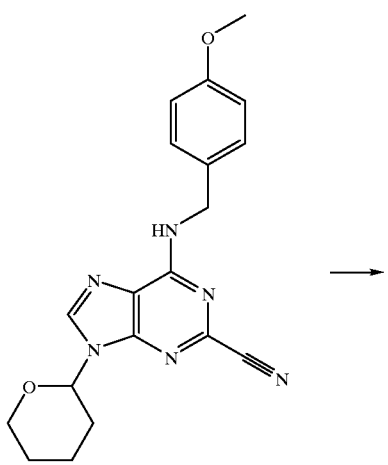

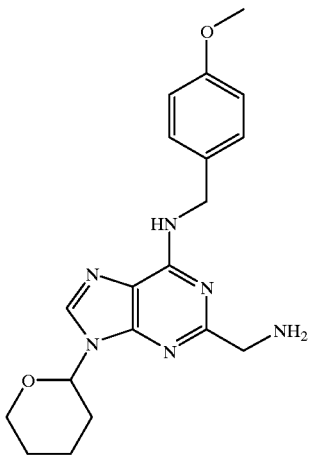

A suspension of 6-[(4-methoxybenzyl)amino]-9-tetrahydro-2H-pyran-2-yl-9H purine-2-carbonitrile (Preparation 18) (3.20 g, 8.78 mmol) in ethanol (250 ml) was saturated with ammonia gas and heated gently until a solution was achieved. This solution was then treated with Raney (trade mark) nickel (0.64 g), pressurised to 414 kPa (60 psi) with hydrogen in a sealed vessel and stirred at 60° C. for 18 hours. TLC analysis showed that some starting material still remained and so further Raney (trade mark) nickel (0.15 g) was added and the mixture again pressurised to 414 kPa (60 psi) with hydrogen in a sealed vessel and stirred at 60° C. for 18 hours. The mixture was cooled and filtered through a pad of Arbocel (trade mark) and the solvent was removed under reduced pressure. The residue was azeotroped with dichloromethane (×2) and then purified by column chromatography on silica gel eluting with dichloromethane:methanol: 0.88 ammonia (97:2.5:0.5 by volume) to afford the title compound as a cream foam (1.65 g).

MS: 369 (MH$^+$)

$^1$H-NMR (CDC$_{13}$) δ: 7.89 (1H, s), 7.28 (2H, d), 6.85 (2H, d), 6.00 (1H, br s), 5.72 (1H, dd), 4.80 (2H, br m), 4.16 (1H, dd), 3.98 (2H, d), 3.76 (4H, m), 2.33 (2H, m), 1.60–2.15 (6H, m).

PREPARATION 20: N({6-[(4-Methoxybenzyl)amino]-9-tetrahydro-2H-pyran-2yl-9H-purin-2-yl)methyl)-2-methyl-1-propanesulfonamide

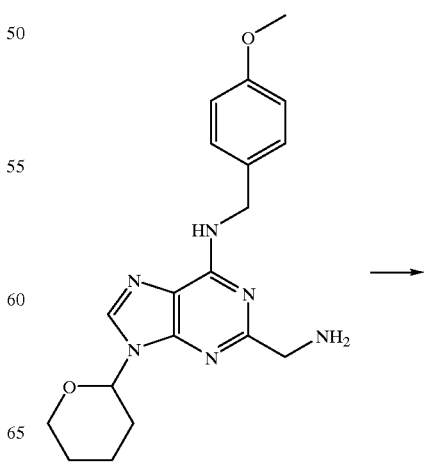

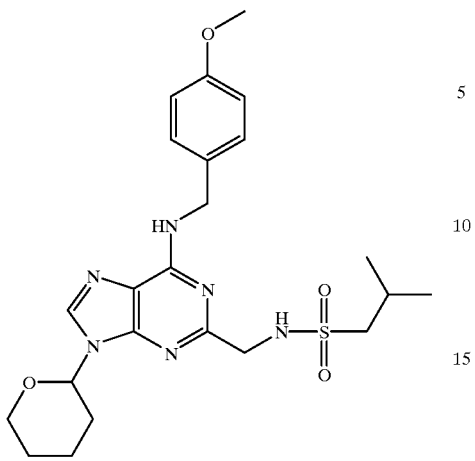

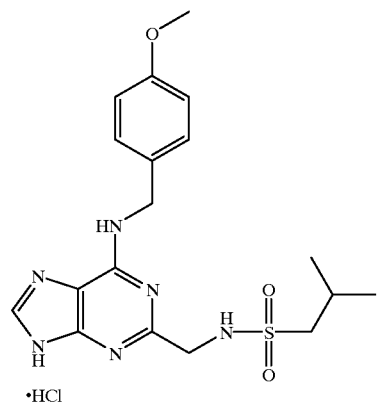

A solution of 2-methyl-1-propanesulfonyl chloride (*J. Prakt. Chem.*, 1979, 321, 107–111) (0.84 g, 5.36 mmol) in dichloromethane (10 ml) was added slowly to a solution of 2-(aminomethyl)-N-(4-methoxybenzyl)-9-tetrahydro-2H-pyran-2-yl-9H-purin-6-amine (Preparation 19) (1.65 g, 4.48 mmol) and triethylamine (1.25 ml, 8.96 mmol) in dry dichloromethane (20 ml) and the resulting mixture was stirred at room temperature under a nitrogen atmosphere for 2 hours. The mixture was washed sequentially with saturated aqueous sodium hydrogen carbonate and brine, dried over anhydrous magnesium sulphate, filtered and evaporated under reduced pressure. The residue was purified by column chromatography on silica gel eluting with dichloromethane:methanol (99:1 by volume) to afford the title compound as a pale yellow foam (1.55 g).

MS: 489 (MH$^+$)

$^1$H-NMR (CDCl$_3$) δ: 7.92 (1H, s), 7.25 (2H, d), 6.84 (2H, d), 6.16 (1H, br s) (1H, dd), 5.60 (1H, t), 4.73 (2H, br m), 4.40 (2H, d), 4.15 (1H, dd), 3.78 (4H, m), 2.97 (2H, d), 2.25 (1H, m), 2.05 (3H, m), 1.78 (3H, m), 1.04 (6H, d).

PREPARATION 21: N-({6-[(4-Methoxybenzyl)amino]-9H-purin-2-yl}methyl)-2-methyl-1-propanesulfonamide hydrochloride A solution of N({6-[(4-methoxybenzyl)amino]-9-tetrahydro-2H-pyran-2-yl-9H-purin-2-yl}methyl)-2-methyl-1-propanesulfonamide (Preparation 20) (1.55 g, 3.17 mmol) in ethanol (100 ml) was treated with hydrochloric acid (2N, 4.5 ml). The mixture was stirred at room temperature for 18 hours, after which time a crystalline precipitate was filtered off, washed with ethanol and dried to afford the title compound as a white solid (1.03 g).

MS: 405 (MH$^+$), 427 (MNa$^+$)

$^1$H-NMR (DMSO-d$_6$) δ: 8.54 (1H, br s), 7.68 (1H, br m), 7.35 (2H, d), 6.87 (2H, d), 4.80 (2H, br m), 4.31 (2H, d), 3.72 (3H, s), 2.91 (2H, d), 2.06 (1H, m), 0.93 (6H, d).

PREPARATION 22: (2R,3R,4S,5S)-4-(Benzoyloxy)-5-[(ethylamino)carbonyl]-12-{[(isobutylsulfonyl)amino]methyl}-6-[(4 methoxybenzyl)amino]-9H-purin-9-yl}tetrahydro-3-furanyl benzoate

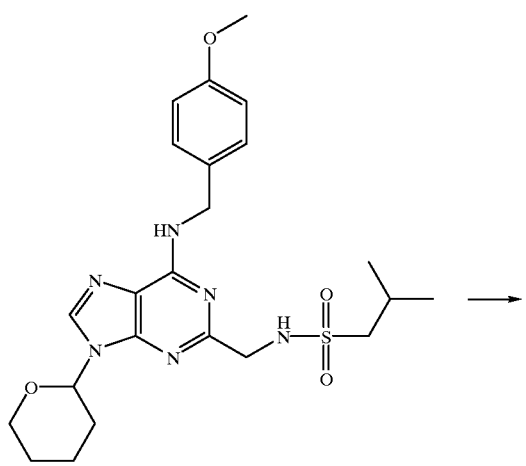

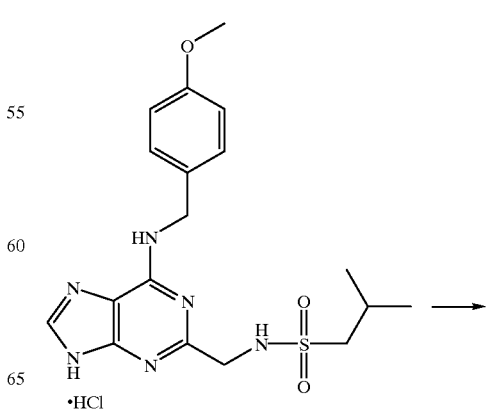

-continued

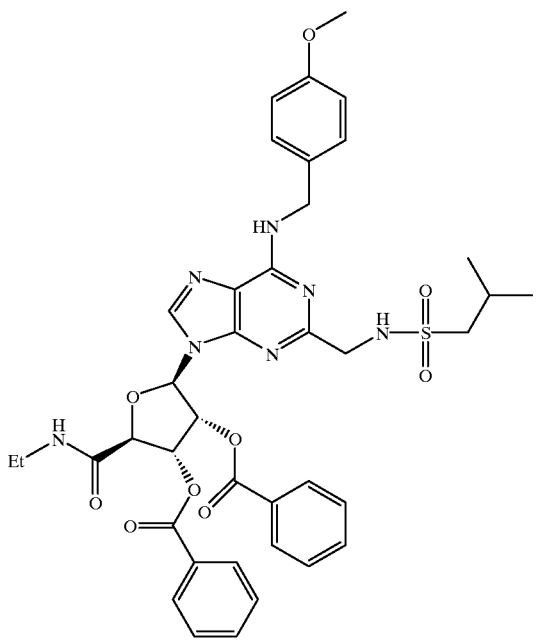

A suspension of N({6-[(4-methoxybenzyl)amino]-9H-pudn-2-yl}methyl)-2-methyl-1-propanesulfonamide hydrochloride (Preparation 21) (0.25 g, 0.57 mmol) in 1,1,1,1,3,3,3-hexamethyldisilazane (10 mi) was heated at reflux under a nitrogen atmosphere for 90 minutes until a solution was obtained. The solution was allowed to cool to room temperature and the solvent was removed under reduced pressure. The residue was azeotroped from dichloromethane and then acetonitrile. The residue was dissolved in acetonitrile (5 ml) and treated with a solution of (2S,3R,4R)-5-(acetyloxy)-4-(benzoyloxy)-2-[(ethyl amino)carbonyl]tetrahydro-3-furanyl benzoate (Preparation 26) (0.30 g, 0.68 mmol) in acetonitrile (5 ml) and trimethylsilyl trifluoromethanesulfonate (0.12 ml, 0.68 mmol). The resulting solution was stirred at room temperature under a nitrogen atmosphere for 19 hours. TLC analysis showed that some starting material still remained and so further trimethylsilyl trifluoromethanesulfonate (0.03 ml, 0.17 mmol) added and the stirring continued for 3 hours. The mixture was diluted with ethyl acetate (20 ml) and washed with saturated aqueous sodium hydrogen carbonate. The organic layer was separated, washed with brine, dried over anhydrous magnesium sulphate, filtered and evaporated under reduced pressure. The residue was purified by column chromatography on silica gel eluting with a gradient system of dichloromethane:methanol (99.5:0.5 by volume) gradually changing to dichloromethane:methanol (99:1 by volume) to afford the title compound as a white foam (245 mg).

MS: 786 (MH$^+$), 808 (MNa$^+$)

$^1$H-NMR (CDCl$_3$) δ: 8.06 (2H, d), 8.00 (1H, s), 7.84 (2H, d), 7.61 (1H, dd), 7.53 (1H, dd), 7.45 (2H, dd), 7.33 (4H, m), 7.05 (1H, m), 6.89 (2H, d), 6.26 (4H, m), 5.71 (1H, t), 4.93 (1H, d), 4.75 (2H, br m), 4.44 (2H, d), 3.80 (3H, s), 3.47 (1H, m), 3.34 (1H, m), 2.91 (2H, t), 2.27 (1H, m), 1.15 (3H, t), 1.04 (6H, d).

PREPARATION 23: (3aS,4S,6R,6aR)-N-ethyl-6-methoxy-2,2-dimethyltetrahydrofuro[3,4-d][1,3]dioxole-4-carboxamide

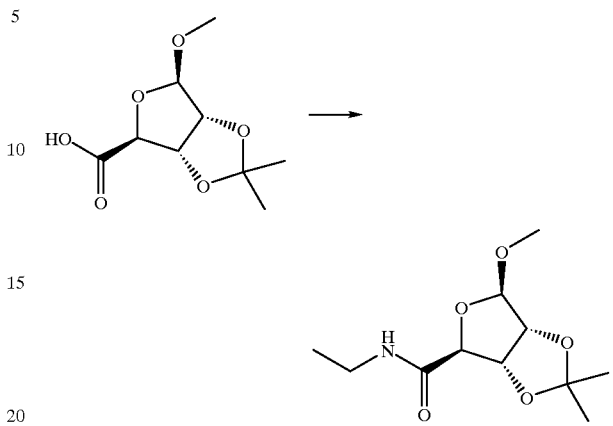

Oxalyl chloride (14.0 ml, 160 mmol) was added dropwise to a stirred solution of (3aR,4S,6R,6aR)-6-methoxy-2,2-dimethyltetrahydrofuro[3,4d][1,3]dioxole-4-carboxylic acid (*J. Amer. Chem. Soc.*, 1958, 80, 5168–5173) (23.30 g, 107 mmol) in anhydrous dichloromethane (120 ml) and N,N-dimethylformamide (2 drops) and the mixture was stirred at room temperature for 3 hours until gas evolution had ceased. TLC analysis showed that some starting material still remained therefore further N,N-dimethylformamide (2 drops) was added and the stirring was continued for 1 hour. The solvent was removed under reduced pressure and the residue azeotroped with anhydrous dichloromethane (×2). The residue was then dissolved in anhydrous dichloromethane (200 ml) and the resulting solution was treated dropwise with ethylamine (2M in tetrahydrofuran, 140 ml, 280 mmol). This solution was left to stand at room temperature for 48 hours. Diethyl ether (250 ml) was added and the mixture was stirred for 15 minutes, filtered and evaporated under reduced pressure. The residue was purified by column chromatography on silica gel eluting with a gradient system of dichloromethane:ethyl acetate (100:0 by volume) gradually changing to dichloromethane:ethyl acetate (44:66 by volume) to afford the title compound as a yellow solid (24.70 g).

MS: 246 (MH$^+$)

$^1$H-NMR (CDCl$_3$) δ: 6.53 (1H, br m), 5.12 (1H, dd), 5.07 (1H, d), 4.60 (1H, d), 4.54 (1H, dd), 3.46 (3H, s), 3.32 (2H, m), 1.51 (3H, s), 1.34 (3H, s), 1.15 (3H, t),

PREPARATION 24: (2S,3S,4-N-ethyl-3,4-dihydroxy-5-methoxytetrahydro-2-furancarboxamide

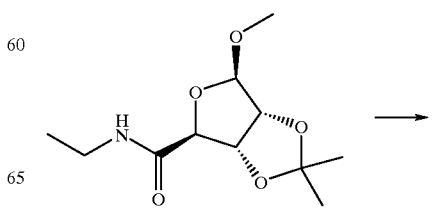

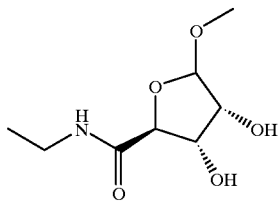

A solution of (3aS,4S,6R,6aR)-N-ethyl-6-methoxy-2,2-dimethyltetrahydrofuro[3,4-d][1,3]dioxole-4-carboxamide (Preparation 23) (24.60 g, 100 mmol) and pyridinium ptoluenesulphonate (2.50 g, 100 mmol) in methanol (500 ml) was heated at reflux for 18 hours. NMR analysis showed that some starting material still remained. The solvent was evaporated under reduced pressure and the residue was dissolved in methanol (500 ml) and heated under reflux for 8 hours. NMR analysis showed that some starting material still remained. The solvent was removed under reduced pressure once more and the residue was dissolved in methanol (500 ml) and heated under reflux for 24 hours. The solvent was then removed under reduced pressure and the residue was azeotroped with dichloromethane (x3) to afford the title compound as an oil (20.50 g).

$^1$H-NMR (CDCl$_3$) δ: 6.58 (1H, br m), 4.99 (0.25H, d), 4.94 (0.75H, d), 4.46 (0.25H, d), 4.37 (1.5H, m), 4.24 (0.25H, dd), 4.05 (1H, m), 3.52 (0.75H, s), 3.47 (2.25H, s), 3.30 (2H, m), 1.16 (3H, m)

PREPARATION 25: (3R,4R,5S)-4-(Benzoyloxy)-5-[(ethylamino)carbonyl]-2-methoxytetrahydro-3-furanyl benzoate

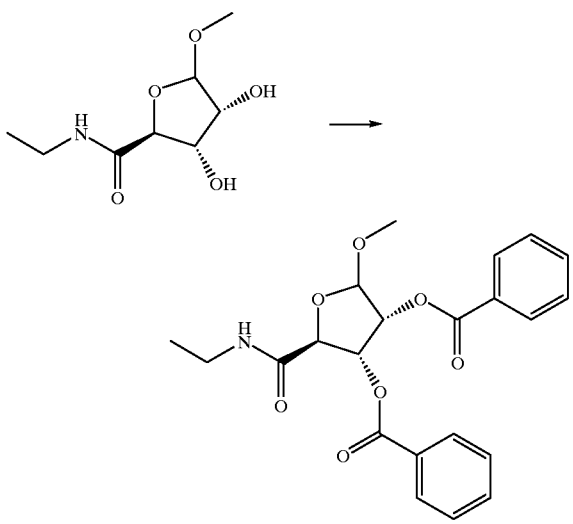

A solution of benzoyl chloride (30.0 ml, 259 mmol) in dichloromethane (100 ml) was added slowly to a solution of (2S,3S,4R)-/ethyl-3,4-dihydroxy-5-methoxytetrahydro-2-furancarboxamide (Preparation 24) (20.50 g, 100 mmol) and pyridine (33.0 ml, 409 mmol) in dichloromethane (400 ml) and the resulting mixture was stirred at room temperature for 18 hours. The solvent was removed under reduced pressure and the residue was partitioned between diethyl ether and hydrochloric acid (1M, 300 ml). The layers were separated and the aqueous layer was re-extracted with diethyl ether. The organic layers were combined, washed sequentially with water and brine, dried over anhydrous magnesium sulphate, filtered and evaporated under reduced pressure. The residue was purified by column chromatography on silica gel eluting with a gradient system of dichloromethane:diethyl ether (95:5 by volume) gradually changing to dichloromethane:diethyl ether (80:20 by volume) to afford the title compound as an oil and as a mixture of α and β anomers (37.0 g).

$^1$H-NMR (CDCl$_3$) δ: 8.16 (0.5H, d), 7.95 (1.5H, d), 7.88 (1.5H, d), 7.81 (0.5H, d), 7.25–7.66 (6H, m), 6.65 (1H, br m), 5.88 (1H, m), 5.60 (0.75H, dd), 5.46 (0.25H, d), 5.23 (0.75H, d), 5.17 (0.25H, t), 4.80 (1H, m), 3.59 (2.25H, s), 3.49 (0.75H, s), 3.39 (2H, m), 1.23 (3H, t).

PREPARATION 26: (2S,3R,4R)-5-(Acetyloxy)-4-(benzoyloxy)-2-[(ethylamino)carbonyl]tetrahydro-3-furanyl benzoate

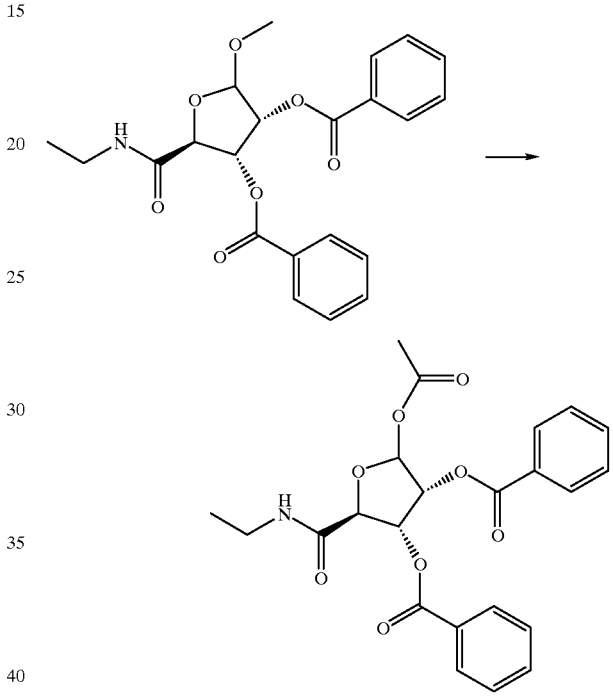

A solution of (3R,4R,5S-4-(benzoyloxy)-5-[(ethylamino)carbonyl]-2-methoxytetrahydro-3-furanyl benzoate (Preparation 25) (37.0 g, 89.6 mmol) in a mixture of acetic acid (330 ml, 5.77 mol) and acetic anhydride (67 ml, 709 mmol) was cooled to −10° C. and treated dropwise with hydrochloric acid (12N, 7.0 ml,132 mmol). The mixture was stirred for 18 hours, during which time it was allowed to warm to room temperature. After re-cooling the mixture to 0° C., water (1000 ml) was added slowly and the mixture was extracted with ethyl acetate (3×500 ml). The organic layers were combined, washed sequentially with water, saturated aqueous sodium hydrogen carbonate and brine, dried over anhydrous magnesium sulphate, filtered and evaporated under reduced pressure. The residue was purified by column chromatography on silica gel eluting with a gradient system of diethyl ether:pentane (66:44) gradually changing to diethyl ether:pentane (100:0). The residue was further purified by column chromatography on silica gel eluting with a gradient system of dichloromethane:diethyl ether (95:5 by volume) gradually changing to dichloromethane:diethyl ether (90:10 by volume) to afford the title compound as a mixture of α- and β-anomers (15.40 g).

$^1$H-NMR (CDCl$_3$) δ: 8.12 (0.8H, d), 7.97 (1.2H, d), 7.92 (1.2H, d), 7.79 (0.8H, d), 7.24–7.65 (6H, m), 6.73 (0.4H, d), 6.62 (0.4H, br m), 6.46 (0.6H, br m), 6.42 (0.6H, d), 6.07

(0.4H, dd), 5.95 (0.6H, t), 5.72 (0.6H, d), 5.44 (0.4H, t), 4.94 (0.4H, d), 4.86 (0.6H, d), 3.36 (2H, m), 2.17 (1.8H, s), 2.10 (1.2H, s), 1.20 (3H, m).

PREPARATION 27: (2S,3S,4R,5R)5-{2-(Aminomethyl)-6-[(2,2-diphenylethyl)amino]-9H-purin-9-yl}-N-ethyl-3,4-dihydroxytetrahydro-2-furancarboxamide

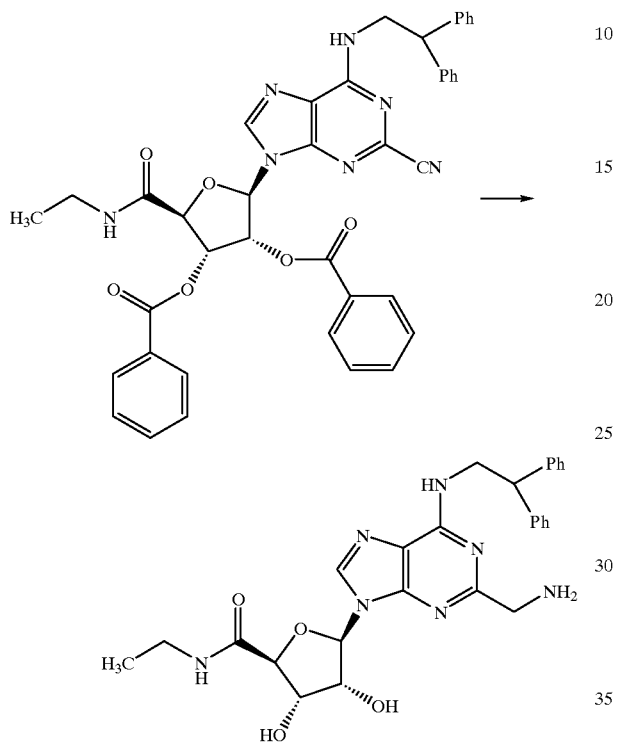

10% w/w Palladium on carbon (400 mg) was added to a solution of (2S,3R,4R,5R)-4-(benzoyloxy)-5-{2-cyano-6-[(2,2-diphenylethyl)amino]-9H-purin-9-yl}-2-[(ethylamino)carbonyl]tetrahydro-3-furanyl benzoate (Preparation 7) (2.09, 2.70 mmol) in ethanol saturated with ammonia (40 ml). The reaction mixture was stirred under an atmosphere of hydrogen (414 kPa, 60 psi) for 16 hours at room temperature, filtered through Arbocel (Trade Mark) and evaporated under reduced pressure. The residue was purified by column chromatography on silica gel eluting with dichloromethane:methanol: 0.88 concentrated aqueous ammonia (95:5:0.5 by volume gradually changing to 90:10:1 by volume) to give the title compound as a solid (1.2 g).

$^1$H-NMR (D$_6$-DMSO) δ: 8.55 (1H, s), 8.45–8.30 (1H, br s), 7.45–7.10 (10H, m), 6.10–6.00 (1H, m),4.70–4.50 (2H, m),4.35–4.10 (6H, m), 3.20–3.05 (2H, m 1.10–0.95 (3H, m).

PHARMACOLOGICAL ACTIVITY

All the compounds of Examples 1–11 were tested for anti-inflammatory activity by their ability to inhibit neutrophil function (which indicates A2a receptor agonist activity) by the method described on page 20 and all had an IC$_{50}$ of less than 1 micromolar.

What is claimed is:
1. A compound of the formula

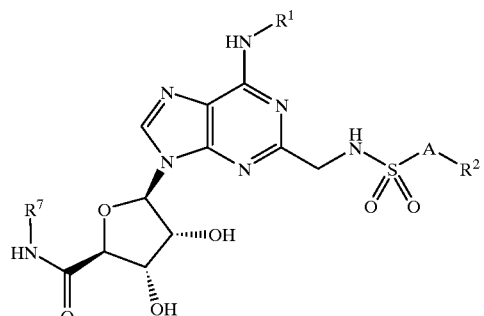

(I)

or a pharmaceutically acceptable salt or solvate thereof, wherein $R^1$ is hydrogen or $C_1$–$C_6$ alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

A is a bond or $C_1$–$C_3$ alkylene;

$R^2$ is (i) hydrogen, $C_1$–$C_6$ alkyl, $C_3$–$C_7$ cycloalkyl, phenyl or naphthyl, said $C_3$–$C_7$ cycloalkyl, phenyl or naphthyl being optionally substituted by $C_1$–$C_6$ alkyl, phenyl, $C_1$–$C_6$ alkoxy-($C_1$–$C_6$)-alkyl, $R^3R^3N$—($C_1$–$C_6$)-alkyl, fluoro-($C_1$–$C_6$)-alkyl, fluoro-($C_1$–$C_6$)-alkoxy, $C_2$–$C_5$ alkanoyl, halo, —OR$^3$, cyano, —COOR$^3$, $C_3$–$C_7$ cycloalkyl, —S(O)$_m$R$^4$, —NR$^3$R$^3$, —SO$_2$NR$^3$R$^3$, —CONR$^3$R$^3$, —NR$^3$COR$^4$ or —NR$^3$SO$_2$R$^4$, with the proviso that $R^2$ is not hydrogen when A is a bond, or (ii) when A is $C_2$–$C_3$ alkylene, —NR$^8$R$^9$, —OR$^3$, —COOR$^3$, —OCOR$^4$, —SO$_2$R$^4$, —CN, —SO$_2$NR$^3$R$^3$, —NR$^3$COR$^4$ or —CONR$^3$R$^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, $R^3R^3N$—($C_1$–$C_6$)-alkyl, fluoro-($C_1$–$C_6$)-alkyl, fluoro-($C_1$–$C_6$)-alkoxy, fluoro-($C_2$–$C_5$)-alkanoyl, halo, cyano, —OR$^5$, R$^6$, —COR$^5$, —NR$^5$R$^5$, —COOR$^5$, —S(O)$_m$R$^6$, —SO$_2$NR$^5$R$^5$, —CONR$^5$R$^5$, —NR$^5$SO$_2$R$^6$ or —NR$^5$COR$^6$ and optionally N-substituted by $C_1$–$C_6$ alkoxy-($C_1$–$C_6$)-alkyl, $R^3R^3N$—($C_2$–$C_6$)-alkyl, fluoro-($C_1$–$C_6$)-alkyl, fluoro-($C_2$–$C_5$)-alkanoyl, R$^6$, —COR$^5$, —COOR$^5$, —S(O)$_m$R$^6$, —SO$_2$NR$^5$R$^5$ or —CONR$^5$R$^5$;

$R^3$ is H, $C_1$–$C_6$ alkyl, $C_3$–$C_7$ cycloalkyl or phenyl;

$R^4$ is $C_1$–$C_6$ alkyl, $C_3$–$C_7$ cycloalkyl or phenyl;

$R^5$ is H, $C_1$–$C_6$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

m is 0, 1 or 2;

"het", used in the definitions of $R^5$ and $R^6$, means C-linked pyrrolyl imidazolyl triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo;

$R^7$ is methyl, ethyl or cyclopropylmethyl; and either, $R^8$ and $R^9$, taken together with the nitrogen atom to which they are attached represent azetidinyl, pyrrolidinyl, piperidinyl, morpholinyl, piperazinyl, homopiperidinyl, homopiperazinyl or tetrahydroisoquinolinyl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^3R^3N$-($C_1$–$C_6$)-alkyl, fluoro-($C_1$–$C_6$)-alkyl, —$CONR^3R^3$, —$COOR^3$ or $C_2$–$C_5$ alkanoyl, and optionally substituted on a ring carbon atom not adjacent to a ring nitrogen atom by fluoro-($C_1$–$C_6$)-alkoxy, halo, —$OR^3$, cyano, —$S(O)_mR^4$, —$NR^3R^3$, —$SO_2NR^3R^3$, —$NR^3COR^4$ or —$NR^3SO_2R^4$, and said piperazin-1-yl and homopiperazin-1-yl being optionally substituted on the ring nitrogen atom not attached to A by $C_1$–$C_6$ alkyl, phenyl, $C_1$–$C_6$ alkoxy-($C_2$–$C_6$)-alkyl, $R^3R^3N$—($C_2$–$C_6$)-alkyl, fluoro-($C_1$–$C_6$)-alkyl, $C_2$–$C_5$ alkanoyl, —$COOR^4$, $C_3$–$C_8$ cycloalkyl, —$SO_2R^4$, —$SO_2NR^3R^3$ or —$CONR^3R^3$, or, $R^8$ is H, $C_1$–$C_6$ alkyl, $C_3$–$C_8$ cycloalkyl, phenyl or benzyl and $R^9$ is H, $C_1$–$C_6$ alkyl, $C_3$–$C_8$ cycloalkyl, phenyl, benzyl, fluoro-($C_1$–$C_6$)-alkyl, —$CONR^3R^3$, —$COOR^4$, $C_2$–$C_5$ alkanoyl or —$SO_2NR^3R^3$.

2. A compound as claimed in claim 1 wherein $R^1$ is hydrogen or $C_1$–$C_6$alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

A is a bond or $C_1$–$C_3$ alkylene;

$R^2$ is (i) hydrogen, $C_1$–$C_6$ alkyl, $C_3$–$C_7$ cycloalkyl, phenyl or naphthyl, said $C_3$–$C_7$ cycloalkyl, phenyl or naphthyl being optionally substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$, —$NR^3R^3$, —$SO_2NR^3R^3$, —$CONR^3R^3$, —$NR^3COR^4$ or —$NR^3SO_2R^4$, with the proviso that $R^2$ is not hydrogen when A is a bond, or (ii) when A is $C_2$–$C_3$ alkylene, —$NR^3R^3$, —$OR^3$, —$COOR^3$, —$OCOR^4$, —$SO_2R^4$, —CN, —$SO_2NR^3R^3$, —$NR^3COR^4$ or —$CONR^3R^3$, or (iii) a C-linked, 4 to 11 membered, mono or bicyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, fluoro-($C_2$–$C_5$)-alkanoyl, halo, cyano, —$OR^3$, $R^6$, —$COR^5$, —$NR^5R^5$, —$COOR^5$, —$S(O)_mR^6$, —$SO_2NR^5R^5$, —$CONR^5R^5$, —$NR^5SO_2R^6$ or —$NR^5COR^6$ and optionally N-substituted by $C_1$–$C_6$ alkoxy-($C_1$–$C_6$)-alkyl, amino-($C_2$–$C_6$)-alkyl, fluoro-($C_1$–$C_6$)-alkyl, fluoro-($C_2$–$C_5$)-alkanoyl, $R^6$, —$COR^5$, —$COOR^5$, —$S(O)_mR^6$, —$SO_2NR^5R^5$ or —$CONR^5R^5$, or (iv) when A is $C_2$–$C_3$ alkylene, N-linked azetidinyl, pyrrolidinyl, piperidinyl or piperazinyl, each being optionally C-substituted by $C_1$–$C_6$ alkyl, phenyl, $C_1$–$C_6$ alkoxy-($C_1$–$C_6$)-alkyl, amino-($C_1$–$C_6$)-alkyl, fluoro-($C_1$–$C_6$)-alkyl, fluoro-($C_1$–$C_6$)-alkoxy, $C_2$–$C_5$ alkanoyl, halo, —$OR^3$, cyano, —$COOR^3$, $C_3$–$C_7$ cycloalkyl, —$S(O)_mR^4$, —$NR^3R^3$, —$SO_2NR^3R^3$, —$CONR^3R^3$, —$NR^3COR^4$ or —$NR^3SO_2R^4$ and optionally N-substituted by $C_1$–$C_6$ alkyl, phenyl, $C_1$–$C_6$ alkoxy-($C_1$–$C_6$)-alkyl, amino-($C_2C_6$)-alkyl, fluoro-($C_1$–$C_6$)-alkyl, $C_2$–$C_5$ alkanoyl, —$COOR^3$, $C_3$–$C_7$ cycloalkyl, —$S(O)_mR^4$, —$SO_2NR^3R^3$ or —$CONR^3R^3$;

$R^3$ is H, $C_1$–$C_6$ alkyl or phenyl;

$R^4$ is $C_1$–$C_6$ alkyl or phenyl;

$R^5$ is H, $C_1$–$C_6$ alkyl, $C_3$–$C_7$ cycloalkyl, phenyl, naphthyl or het;

$R^6$ is $C_1$–$C_6$ alkyl, $C_3$–$C_7$ cycloalkyl, phenyl, naphthyl or het;

m is 0, 1 or 2;

"het", used in the definitions of $R^5$ and $R^6$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, quinolinyl, isoquinolinyl, benzimidazolyl, quinazolinyl, phthalazinyl, benzoxazolyl or quinoxalinyl, each optionally substituted by $C_1$–$C_6$ alkyl, $C_1$–$C_6$ alkoxy, cyano or halo; and $R^7$ is methyl, ethyl or cyclopropylmethyl.

3. A compound as claimed in claim 1 or claim 2 wherein A is a bond.

4. A compound as claimed in claim 1 or claim 2 wherein A is $C_1$–$C_3$ alkylene.

5. A compound as claimed in claim 1 wherein A is $C_2$–$C_3$ alkylene.

6. A compound as claimed in claim 5 wherein A is —$CH_2CH_2$—.

7. A compound as claimed in claim 2 wherein $R^2$ is $C_1$–$C_6$ alkyl, phenyl or naphthyl, said phenyl being optionally substituted by phenyl.

8. A compound as claimed in claim 7 wherein $R^2$ is methyl, n-propyl, isopropyl, 2-methylprop-1-yl, phenyl, 4-phenylphenyl, 1-naphthyl or 2-naphthyl.

9. A compound as claimed in claim 6 wherein $R^2$ is —$NR^8R^9$, $R^8$ and $R^9$ being as defined in claim 1.

10. A compound as claimed in claim 9 wherein $R^8$ and $R^9$ taken together with the nitrogen to which they are attached represent piperidinyl.

11. A compound as claimed in claim 1 wherein —A—$R^2$ is methyl, n-propyl, isopropyl, 2-methylprop-1-yl, phenyl, 4-phenylphenyl, phenylmethyl, 1-naphthyl, 2-naphthyl or 2-(piperidin-1-yl)ethyl.

12. A compound as claimed in claim 2 wherein $R^1$ is $C_1$–$C_6$ alkyl substituted by 1 or 2 phenyl group(s), said phenyl group(s) being optionally substituted by $C_1$–$C_6$ alkoxy.

13. A compound as claimed in claim 12 wherein $R^1$ is 2,2-diphenylethyl or (4-methoxyphenyl)methyl.

14. A compound as claimed in claim 1 which is selected from the group consisting of:

(2S,3S,4R,5R)-5-{2-{[(benzylsuffonyl)amino]methyl}-6-[(2,2-diphenylethyl)amino]-9H-purin-9-yl}-N-ethyl-3,4-dihydroxytetrahydro-2-furancarboxamide;

(2S,3S,4R,5R)-5-(6-[(2,2-diphenylethyl)amino]-2-{[(propylsulfonyl)amino]methyl}-9H-purin-9-yl)-N-ethyl-3,4-dihydroxytetrahydro-2-furancarboxamide;

(2S,3S,4R,5R)-5-(6-[(2,2-diphenylethyl)amino]-2-{[(isopropylsulfonyl)amino]methyl}-9purin-9-yl)-N-ethyl-3,4-dihydroxytetrahydro-2-furancarboxamide;

(2S,3S,4R,5R5-(6-[(2,2-diphenylethyl)amino]-2-{[(phenylsulfonyl)amino]methyl}-9H-purin-9-yl)-N-ethyl-3,4-dihydroxytetrahydro-2-furancarboxamide;

(2S,3S,4R,5R)-5-2-{[([1,1'-biphenyl]-4-ylsulfonyl)amino]methyl}-6-[(2,2-diphenylethyl)amino]-9H-purin-9-yl)-N-ethyl-3,4-dihydroxytetrahydro-2-furancarboxamide;

(2S,3S,4R,5R)-5-(6-[(2,2-diphenylethyl)amino]-2-{[(1-naphthylsulfonyl)amino]methyl}-9H-purin-9-yl)-N-ethyl-3,4-dihydroxytetrahydro-2-furancarboxamide;

(2S,3S,4R,5R)-5-(6-[(2,2-diphenylethyl)amino]-2-{[(2-naphthylsulfonyl)amino]methyl)-9H-purin-9-yl)-N-ethyl-3,4-dihydroxytetrahydro-2-furancarboxamide;

(2S,3S,4R,5R)-5-(6-[(2,2-diphenylethyl)amino]-2-{[(methylsulfonyl)amino]methyl}-9H-purin-9-yl)-N-ethyl-3,4-dihydroxytetrahydro-2-furancarboxamide;

(2S,3S,4R,5R)-5-(6-[(2,2-diphenylethyl)amino]-2-{[(isobutylsulfonyl)amino]methyl}-9H-purin-9-yl)-N-ethyl-3,4-dihydroxytetrahydro-2-furancarboxamide;

(2S,3S,4R,5-N-ethyl-3,4-dihydroxy-5-2-{[(isobutylsulfonyl)amino]methyl}-6-[(4-methoxybenzyl)amino]-9H-purin-9-yl}tetrahydro-2-furancarboxamide; and (2S,3S,4R,5R)-5-{6-[(2,2-diphenylethyl)amino]-2-[({[2-(1-piperidinyl)ethyl]sulfonyl}amino)methyl]-9H-purin-9-yl}-N-ethyl-3,4-dihydroxytetrahydro-2-furancarboxamide;

and the pharmaceutically acceptable salts and solvates thereof.

15. A pharmaceutical composition comprising a compound of the formula (I) or a pharmaceutically acceptable salt or solvate thereof, as claimed in claim 1, together with a pharmaceutically acceptable excipient, diluent or carrier.

16. A method of treatment of a mammal, including a human being, having a disease for which an A2a receptor agonist is indicated, comprising treating said mammal with an effective amount of a compound of the formula (I) or a pharmaceutically acceptable salt or solvate thereof as claimed in claim 1, or with a pharmaceutical composition containing said compound as claimed in claim 15.

17. A method of treatment of a mammal, including a human being, having an inflammatory disease, comprising treating said mammal with an effective amount of a compound of the formula (I) or a pharmaceutically acceptable salt or solvate thereof as claimed in claim 1, or with a pharmaceutical composition containing said compound as claimed in claim 15.

18. A method of treatment of a mammal, including a human being, having a respiratory disease, comprising treating said mammal with an effective amount of a compound of the formula (I) or a pharmaceutically acceptable salt or solvate thereof as claimed in claim 1, or with a pharmaceutical composition containing said compound as claimed in claim 15.

19. A method as claimed in claim 18 where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

20. A method of treatment of a mammal, including a human being, having septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, allergic dermatitis, eczema, ulcerative colitis, Crohn's disease, inflammatory bowel disease, *Heliobacter pylori*-gastritis, non-*Heliobacter pylori*-gastritis, non-steroidal anti-inflammatory drug-induced damage to the gastrointestinal tract, a psychotic disorder, or in need of wound healing, comprising treating said mammal with an effective amount of a compound of the formula (I) or a pharmaceutically acceptable salt or solvate thereof as claimed in claim 1, or with a pharmaceutical composition containing said compound as claimed in claim 15.

21. A process for the preparation of a compound of the formula (I), as claimed in claim 1 or claim 2, or a pharmaceutically acceptable salt or solvate thereof, comprising the following Steps:

(a) deprotection of a compound of the formula (II):

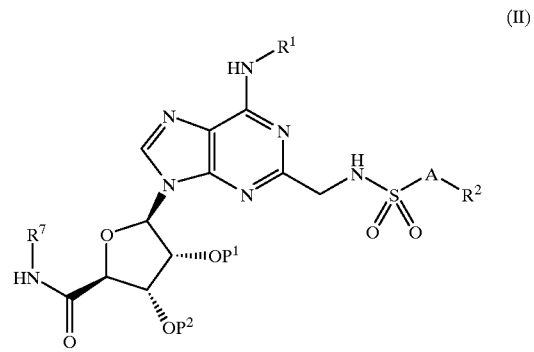

wherein $R^1$, $R^2$, $R^7$ and A are as defined in claim 1 or claim 2 and either (a) $P^1$ and $P^2$ when taken separately, are protecting groups, or (b) $P^1$ and $P^2$, when taken together are a protecting group; the protecting groups $P^1$ and $P^2$, when taken separately, being removed either together or sequentially; or (b sulphonylation of a compound of the formula (XIX):

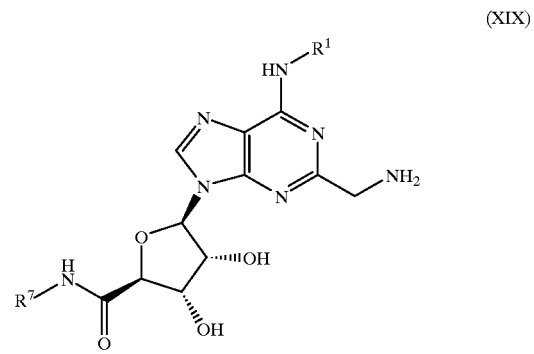

wherein $R^1$ and $R^7$ are as defined in claim 1 or claim 2, with a compound of the formula (VII):

$$R^2—A—SO_2—X \qquad (VII)$$

wherein X is a leaving group $R^2$ and A are as defined in claim 1 or claim 2;

any one of said Steps (a) or (b) being optionally followed by the conversion of a compound of the formula (I) to a pharmaceutically acceptable salt thereof.

22. A process for the preparation of a compound of the formula (I), as claimed in claim 1, in which A is —CH$_2$CH$_2$— and $R^2$ is —NR$^8$R$^9$, or a pharmaceutically acceptable salt or solvate thereof, comprising the reaction of a compound of the formula (XX):

(XX)

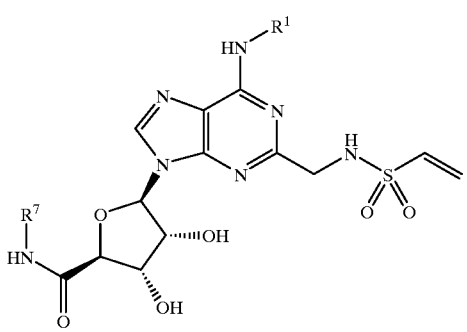

wherein R¹ and R⁷C are as defined in claim 1, With a compound of the formula (XXI):

R⁸R⁹NH    (XXI)

wherein R⁸ and R⁹ are as defined in claim 1;
said process being optionally followed by the conversion of a compound of the formula (I) to a pharmaceutically acceptable salt thereof.

23. A compound of the formula (II):

(II)

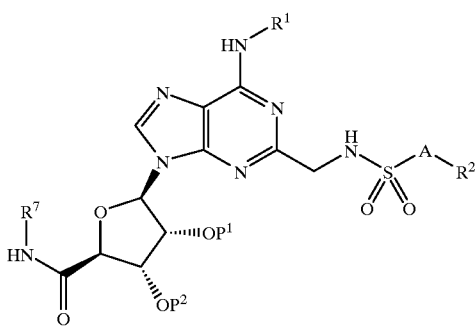

wherein either (a) P¹ and P², when taken separately, are protecting groups or, (b) P¹ and P², when taken together, are a protecting group; or
a compound of the formula (IV), (V), (VI), or (XIV):

(IV)

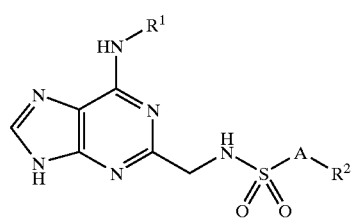

(V)

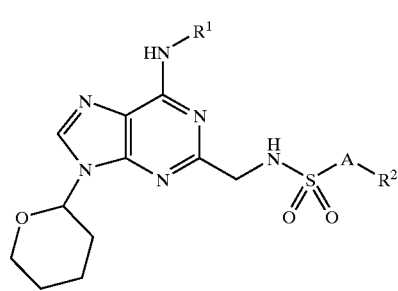

(VI)

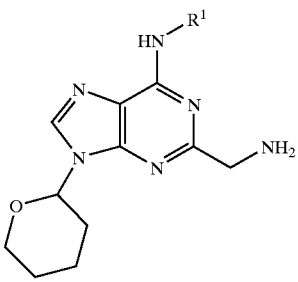

(XIV)

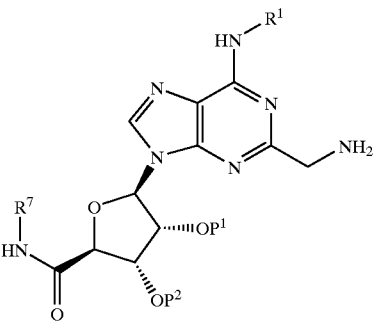

wherein either (a) P¹ and P², when taken separately, are protecting groups, or (b) when taken together, are a protecting group; or
a compound of the formula (XV):

(XV)

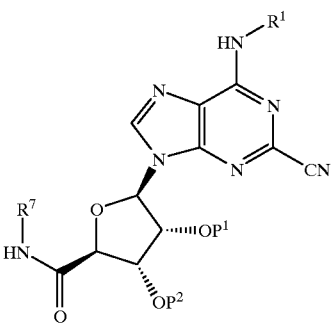

wherein either (a) P¹ and P², when taken separately, are protecting groups, or (b) when taken together, are a protecting group and P³ is a protecting group; or
a compound of the formula (XIX):

(XIX)

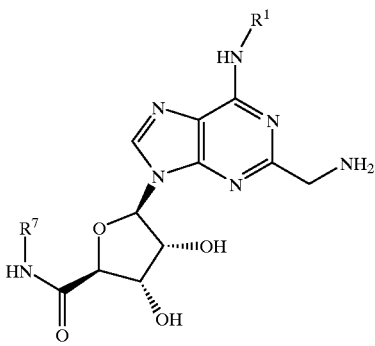

wherein for the formulas (II), (IV), (V), (VI), (XIV), (XV), and (XIX) above, the groups $R^1$, $R^2$, $R^7$ and A are as defined in claim 1 or claim 2.

24. A compound of the formula (VIII):

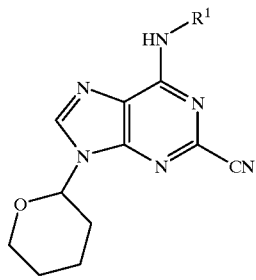

(VIII)

wherein the group $R^1$ is defined as $C_1$–$C_6$ alkyl optionally substituted by 1 or 2 substituents each independently selected from the group consisting of phenyl and naphthy, where said phenyl or naphthyl is optionally substituted by $C_1$–$C_6$ alkyl, $C_1$–$C_6$ alkoxy, halo or cyano.

25. A compound of the formula (XX):

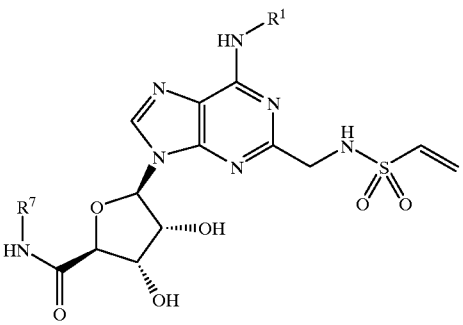

(XX)

wherein the groups $R^1$ and $R^1$ are as defined in claim 1.

* * * * *